(12) United States Patent
Kim et al.

(10) Patent No.: US 10,626,373 B2
(45) Date of Patent: Apr. 21, 2020

(54) CULTURE SCAFFOLD FOR ENHANCING DIFFERENTIATION OF OSTEOBLAST USING PATTERN

(71) Applicants: Seoul National University R&DB Foundation, Seoul (KR); Chang su Kim, Seoul (KR)

(72) Inventors: Hang-Rae Kim, Seoul (KR); Jin-Hee Kim, Chungcheongbuk-do (KR); Bokyung Kim, Chungcheongnam-do (KR); Youn Sang Kim, Gyeonggi-do (KR); Chang su Kim, Seoul (KR)

(73) Assignee: Seoul National University R&DB Foundation, Seoul (KR)

( * ) Notice: Subject to any disclaimer, the term of this patent is extended or adjusted under 35 U.S.C. 154(b) by 59 days.

(21) Appl. No.: 15/644,368

(22) Filed: Jul. 7, 2017

(65) Prior Publication Data

US 2018/0066230 A1 Mar. 8, 2018

(30) Foreign Application Priority Data

Jul. 8, 2016 (KR) ........................ 10-2016-0087090

(51) Int. Cl.
| | | |
|---|---|---|
| *C12N 5/077* | (2010.01) | |
| *C12M 1/00* | (2006.01) | |
| *C12M 1/12* | (2006.01) | |
| *C12M 3/00* | (2006.01) | |

(52) U.S. Cl.
CPC ............ *C12N 5/0654* (2013.01); *C12M 3/00* (2013.01); *C12M 23/02* (2013.01); *C12M 23/20* (2013.01); *C12M 25/14* (2013.01); *C12N 2502/13* (2013.01); *C12N 2506/1384* (2013.01); *C12N 2535/00* (2013.01)

(58) Field of Classification Search
None
See application file for complete search history.

(56) References Cited

FOREIGN PATENT DOCUMENTS

KR 10-2016-0000576 A 1/2016

OTHER PUBLICATIONS

Matsuzaka et al, Biomaterials, 1999, vol. 20, pp. 1293-1301. (Year: 1999).*
Abagnale et al, "Surface topography enhances differentiation of mesenchymal stem cells towards osteogenic and adipogenic lineages" Biomaterials, 2015, 61, 316-326. (Year: 2015).*
Lee et al, "The effect of surface microgrooves and anodic oxidation on the surface characteristics of titanium and the osteogenic activity of human peridontal ligament cells" Archives of Oral Biology, 2013, 58, 59-66. (Year: 2013).*
Song et al, "Cultivation and identification of rat bone marrow-derived mesenchymal stem cells" Molecular Medicine Reports, 2014, 10: 755-760. (Year: 2014).*
Yu et al, "Regulation of Periodontal Ligament Cell Behavior by Cyclic Mechanical Loading and Substrate Nanotexture" Journal of Periodontology; Oct. 2013; 84(10): 1504-1513. (Year: 2013).*
Zhang et al, "Enhanced osteogenic differentiation of MC3T3-E1 cells on grid-topographic surface and evidence for involvement of YAP mediator". Journal Biomedical Materials Research Part A, May 2016 , 104A:1143-1152. (Year: 2016).*
Bastidas-Coral A. P., et al., "Cytokines TNF-α , IL-6, IL-17F, and IL-4 Differentially Affect Osteogenic Differentiation of Human Adipose Stem Cells," Stem Cells International, vol. 2016, p. 1-9 (Aug. 16, 2016), all pages.
Cheng et al., "Additively Manufactured 3D Porous Ti—6Al—4V Constructs Mimic Trabecular Bone Structure and Regulate Osteoblast Proliferation, Differentiation and Local Factor Production in a Porosity and Surface Roughness Dependent Manner," Biofabrication, vol. 6, p. 1-12 (Oct. 7, 2014), all pages.
Toworfe G. K. et al., "Elastic Membrane that Undergoes Mechanical Deformation Enhances Osteoblast Cellular Attachment and Proliferation," International Journal of Biomaterials, vol. 2010, p. 1-10 (Apr. 16, 2010), all pages.
Chang-Su Kim et al. Controlling the osteoblastic differentiation using nano- and micro-scale grooved patterns, Korean Association of Orthodontists 48th Annual Scientific Congress, Oct. 29-31, 2015, the Kimdaejung Convention Center, Gwangju, South Korea.
Chang-Su Kim, A Dissertation Submitted to the Department of Dentistry at the Graduate School of Yonsei University in partial fulfillment of the requirements for the degree of Doctor of Philosophy of Dentistry entitled "Effect of topographical nanopatterning on osteoblastic differentiation" Jul. 2015.

\* cited by examiner

*Primary Examiner* — Allison M Fox
(74) *Attorney, Agent, or Firm* — Faegre Drinker Biddle & Reath LLP

(57) ABSTRACT

The present disclosure relates to a culture scaffold for promoting differentiation from stem cells or precursor cells into osteoblasts, in which the culture scaffold includes a structure composed of a ridge and a groove, a kit using the culture scaffold, and a method for differentiating stem cells or precursor cells into osteoblasts. The culture scaffold of the present disclosure has an optimal pattern depending on the type of stem cells or precursor cells, thereby improving the osteoblast differentiation potency. In particular, it has a feature of showing excellent osteoblast differentiation potency even if only a small amount of supplementary factors inducing osteoblast differentiation is added. Furthermore, since the osteoblast differentiation potency is not greatly influenced by the change in cell density, it is possible to induce differentiation into osteoblasts without being influenced by the inflammatory environment formed by the inflammatory factors that increase upon cell differentiation. Thus, there is an advantage in that the differentiation efficiency into osteoblasts is high. Accordingly, the culture scaffold of the present disclosure having excellent bone regeneration ability can be utilized in various biomedical and medical fields such as dental implants, artificial joints and trauma fixation devices.

7 Claims, 27 Drawing Sheets
(27 of 27 Drawing Sheet(s) Filed in Color)
Specification includes a Sequence Listing.

CULTURE SCAFFOLD FOR ENHANCING DIFFERENTIATION OF OSTEOBLAST USING PATTERN

CROSS-REFERENCE TO RELATED APPLICATIONS

This application claims the benefit of Korean Patent Application No. 10-2016-0087090, filed on Jul. 08 2016, the disclosure of which is incorporated by reference herein for all purposes in its entirety.

TECHNICAL FIELD

The present disclosure relates to a culture scaffold for promoting osteoblasts differentiation from stem cells or precursor cells including a ridge and a groove, in which the culture scaffold includes the structure composed of a ridge and a groove, a kit using the culture scaffold, and a method for differentiating stem cells or precursor cells into osteoblasts.

BACKGROUND

Osteoblasts are differentiated from stem cells of various origins. It is known that various factors are involved in the differentiation of osteoblasts, and in particular, mechanical stress is known to be an important mechanism for osteoblast differentiation. In recent years, considerable efforts have been put into differentiating osteoblast using stem cell differentiation-induction technology under in vitro culture conditions and enhancing the function of bone tissue or treating damage using the same. Accordingly, the technical development is actively being made to induce the differentiation of osteoblasts using stem cells and to utilize the same as a therapeutic agent.

In particular, unlike physiological bone remodeling, bone regeneration under pathological condition such as trauma or the insertion of a prosthesis is accompanied by inflammation. There is currently a method of coating the surface of substances or randomly applying a change to induce bone formation in a dental implant, an orthopedic hip and knee joint, and a trauma fixation device. However, this method is a very limited approach to induce effective bone formation, and in particular, attempts to inhibit osteoblast formation in an inflammatory environment have rarely been made. Accordingly, in the traumatic or inflammatory environment, the effective differentiation induction technology of osteoblasts is very important for the shortening of the treatment period of a patient and the recovery thereof, and can dramatically improve the quality of life of the patient. To this end, currently, osteogenesis inducing factors (osteogenic factors) such as bone morphogenetic protein-4 (BMP-4) have been used, but there is a disadvantage in that they are costly and they have not been studied for improving osteoblasts under inflammatory conditions.

Accordingly, there is a need to study a culture scaffold for effectively differentiating precursor cells of osteoblasts into osteoblasts. In particular, there is a growing need for a culture scaffold capable of effectively inducing osteoblast differentiation even in a traumatic or inflammatory environment.

In this regard, the present inventors have confirmed that, even under conditions in which an inflammatory factor is present or in limited osteogenic factors, precursor cells of various origins can be effectively differentiated into osteoblasts by a culture scaffold composed of the optimized patterns according to the type of precursor cells of osteoblasts, and completed the present disclosure.

SUMMARY

It is an object of the present disclosure to provide a culture scaffold for promoting osteoblasts differentiation from stem cells or precursor cells including a ridge and a groove, and a kit for promoting osteoblast differentiation including the culture scaffold.

It is another object of the present disclosure to provide a method for differentiating stem cells or precursor cells into osteoblasts using the culture scaffold.

It is another object of the present disclosure to provide a method for preparing a culture scaffold for promoting differentiation from stem cells or precursor cells to osteoblasts.

In order to achieve the above object, the present disclosure provides a culture scaffold for promoting differentiation from stem cells or precursor cells into osteoblasts, in which the culture scaffold includes a structure composed of a ridge and a groove.

In addition, the present disclosure provides a kit for promoting osteoblast differentiation including the culture scaffold.

In addition, the present disclosure provides a method for differentiating stem cells or precursor cells into osteoblasts, in which the method includes: (a) inoculating and culturing stem cells or precursor cells in the culture scaffold; and (b) differentiating the cultured stem cells or precursor cells into osteoblasts, in which the stem cells or precursor cells are differentiated into osteoblasts.

In addition, the present disclosure provides a method for preparing a culture scaffold for promoting differentiation from stem cells or precursor cells into osteoblasts, in which the method includes: (a) preparing a mold composed of a ridge and a groove; (b) preparing a negative mold from the mold; and (c) preparing a polymer, which is a culture scaffold, from the negative mold.

The culture scaffold of the present disclosure has an optimal pattern depending on the type of stem cells or precursor cells, thereby improving the differentiation potency into osteoblasts. In particular, it has a feature of showing excellent osteoblast differentiation potency even if only a small amount of supplementary factors inducing osteoblast differentiation is added. Furthermore, the potency of osteoblast differentiation is not greatly influenced by the reduced cell density and by the inflammatory factors that inhibit osteoblast differentiation. Thus, there is an advantage in that the differentiation efficiency into osteoblasts is high. Accordingly, the culture scaffold of the present disclosure having excellent bone regeneration ability can be utilized in various biomedical and medical fields such as dental implants, artificial joints and trauma fixation devices.

BRIEF DESCRIPTION OF THE DRAWINGS

This patent file contains at least one drawing executed in color. Copies of this patent with color drawing(s) will be provided by the Office upon request and payment of the necessary fee.

FIG. 11A illustrates the expression levels of Runx2 (runt-related transcription factor 2), ALPL (alkaline phosphatase gene), SP7 (osterix), BGLAP (osteocalcin), and PIAS (protein inhibitor of activated STAT).

FIG. 11B illustrates the expression levels of COL1A1 (type I collagen).

DETAILED DESCRIPTION

Hereinafter, the present disclosure will be described in detail.

As an example, the present disclosure provides a culture scaffold for promoting osteoblast differentiation from stem cells or precursor cells, in which the culture scaffold includes a structure composed of a ridge and groove.

In addition, as another example, the present disclosure provides a kit for promoting osteoblast differentiation including the culture scaffold.

In the present disclosure, the term "ridge" refers to the portion in which the largest displacement occurs in an embossing manner, and the term "groove" refers to a groove portion in which the largest displacement occurs in an engraving manner.

Figure 1:
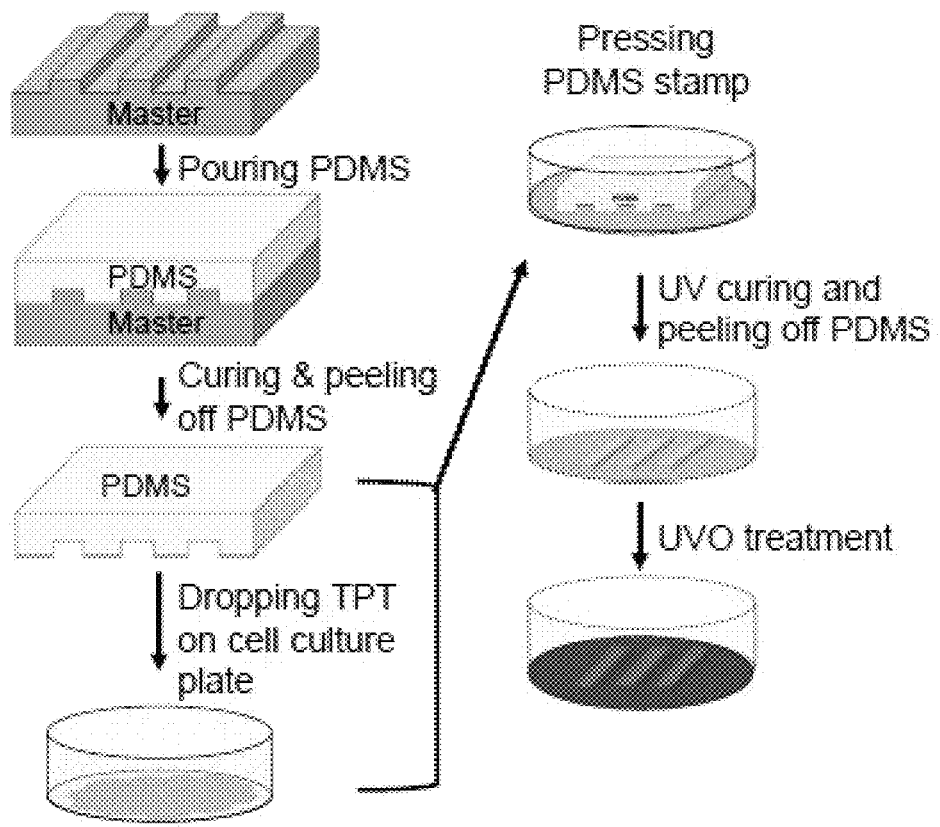
FIG. 1 represents a diagram illustrating a method for preparing a scaffold having a ridge and groove pattern.

In the present disclosure, the term "structure composed of a ridge and a groove" refers to a structure having a pattern in which a ridge and a groove are formed at regular intervals on a flat surface, and the specific shape of a ridge and a groove can be confirmed in FIG. 1.

In the case of having the ridge and the groove according to the following mathematical equations 1 to 3, the relationship can be derived from the osteoclast formation result as a function. At this time, the present disclosure is characterized in that in case of having a ridge and groove pattern of Mathematical Equation 1 as for osteoblast precursor cells, a ridge and groove pattern of Mathematical Equation 2 as for mesenchymal stem cells, and a ridge and groove pattern of Mathematically Equation 3 as for periodontal ligament stem cells, it has the optimal osteoblast differentiation potency. (f(x, y) value is an osteoclast formation result value, x is the width of a ridge, and y is the width of a groove.)

$$\begin{aligned}f_{MC3T3}(x, y) = &\ 48 - 282.3743010506538x + \\ &\ 150.0643654964519x^2 - \\ &\ 2.157836657151817x^3 + \\ &\ 106.00507418528939y + \\ &\ 47.057707899876796xy - \\ &\ 38.1698690150136x^2y + \\ &\ 5.799343765475734y^2 - \\ &\ 5.725807288851501xy^2 + \\ &\ 1.5469548619315638y^3\end{aligned} \quad \text{[Mathematical Equation 1]}$$

-continued $$f_{Ad-MSC}(x, y) = 52.5 - 186.0249972891292x + \\ 420.16867225946131x^2 + \\ 0.23413346166748633x^3 + \\ 113.62075782914779y - \\ 347.796009555016xy - \\ 141.0900051731596x^2y + \\ 48.29374156278727y^2 + \\ 136.97784948772315xy^2 - \\ 27.854120044852811y^3$$ [Mathematical Equation 2]

$$f_{PDLSC}(x, y) = 29 - 276.24302367019254x + \\ 374.7159612153953x^2 + \\ 2.8905955003780566x^3 + \\ 205.73031785654726y - \\ 217.53411649652557xy - \\ 141.83277489850784x^2y - \\ 44.936421391088395y^2 + \\ 131.99978088607176xy^2 - \\ 1823963669842127y^3.$$ [Mathematical Equation 3]

Specifically, in the present disclosure, the width of a ridge is 0.1 to 5 μm and the width of a groove is 0.5 to 7 μm, and more preferably, the width of a ridge is 0.5 to 4 μm and the width of a groove is 1.1 to 6 μm, but is not limited thereto.

In the present disclosure, the numerical value may vary depending on the type of cells that initiates the osteoblast differentiation in the culture scaffold. Specifically, the present disclosure is not limited by the following values. For osteoblast precursor cells, however, the widths of a ridge and a groove may be 0.1 to 3 μm and 1.5 to 7 μm, respectively, preferably 0.5 to 2.83 μm and 1.1 to 6 μm, respectively, and more preferably 0.5 to 2 μm and 1.8 to 4 μm, respectively. For mesenchymal stem cells, the widths of a ridge and a groove may be 0.1 to 3 μm and 0.76 to 7 μm, respectively, preferably 0.5 to 2.83 μm and 1.1 to 6 μm, respectively, and more preferably 0.5 to 2 μm and 1.8 to 4 μm, respectively. In addition, for periodontal ligament stem cells, the widths of a ridge and a groove may be 0.5 to 5 μm and 1.5 to 7 μm, respectively, preferably 1 to 4 μm and 2 to 6 μm, respectively, and more preferably 2 to 2.83 μm and 2 to 6 μm.

In the present disclosure, the term "stem cell" refers to a cell capable of self-replicating and differentiating into two or more cells, and is broadly classified into a totipotent stem cell, a pluripotent stem cell, and a multipotent stem cell. In addition, the stem cells may be classified in a broad sense according to the origin thereof. The stem cell of the present disclosure may be derived from bone marrow, fat, muscle, nerve, skin, tooth, dental tissue, blood, cord blood, liver, gastrointestinal tract, amniotic membrane, placenta or umbilical cord, and preferably, it may be derived from bone marrow, but is not limited thereto.

In the present disclosure, the term "precursor cell" refers to a cell at a stage prior to the establishment of the shape and function of a specific cell, which is also referred to as a committed stem cell. Therefore, it is preferable to use precursor cells of osteoblasts according to the present disclosure for regenerating bone through osteoblast differentiation.

In the present disclosure, the term "osteoblast" refers to a cell having the ability to calcify bone tissues by synthesizing and secreting bone matrix and depositing inorganic salts such as calcium and magnesium ions on the substrate, and can be seen in the region where a new bone is produced by ossification, etc.

In the present disclosure, the term "differentiation" is a phenomenon in which the mutual structure and function are specialized while cells are growing by proliferation, and refers to the shape or function changed to perform the works given to each of the cells, tissues, etc. of an organism. In addition, the term "osteoblast differentiation" is a concept including all of a process of forming a bone matrix by differentiating precursor cells that appear during a process of developing animals, and forming a bone matrix during a process of osteogenesis, which is a series of physiological reactions that form a groove by calcifying the formed bone matrix, or a process of forming a bone matrix by inducing the differentiation of animal stem cells naturally or artificially.

In the present disclosure, the term "culture scaffold" is a concept including a fixture used for culturing cells in a broad sense, and refers to a polymer itself having a ridge and groove pattern engraved for the purpose of the present disclosure, but the present disclosure is not limited thereto.

The substance of the culture scaffold may preferably be trimethylolpropane propoxylate triacrylate (TPT), tripropylene glycol diacrylate (TPD), triethylene glycol dimethacrylate (TGD), triarylcyanate (TAC), trimethylolpropane trimethacrylate (TPTM), polycaprolactone (PCL), collagen, gelatin, hyaluronic acid, keto acid, laminin, keratin, alginate, fibronectin, polyglycolic acid (PGA), poly lactic acid (PLA), polylactic acid-glycolic acid copolymer (PLGA), polyamino acid, polyanhydride, polyorthoester or polyurethane, and more preferably TPT, but is not limited thereto. In addition, the culture scaffold may be coated with titanium (Ti), aluminum (Ai), vanadium (V), titanium alloy (Ti-6Ai-4V), stainless steel (316L), cobalt alloy (Co—Cr—Mo) or nickel-titanium alloy (NiTi), more preferably a titanium-coated substance, and any substance that does not exhibit cytotoxicity even when inserted into living organisms without any limitation. At this time, for the purpose of the present disclosure, the coated substance itself may be used as a culture scaffold after a polymer is separated from the coated substance.

To sum up, the substance of the culture scaffold of the present disclosure may be a polymer, a polymer coated with metal, or metal itself, and specifically one or more of them selected from a group consisting of TPT, TDP, TGD, TAC, TPTM, PCL, collagen, gelatin, hyaluronic acid, keto acid, laminin, keratin, alginate, fibronetin, polyglycolic acid, poly lactic acid, polylactic acid-glycolic acid copolymer, polyamino acid, polyanhydride, polyorthoester, polyurethane, titanium (Ti), aluminum (Ai), vanadium (V), titanium alloy (Ti-6Ai-4V), stainless steel (316L), cobalt alloy (Co—Cr—Mo) and nickel-titanium alloy (NiTi), but is not limited thereto.

In the present disclosure, the culture scaffold can induce osteoblast differentiation even if only a small amount of supplementary factors inducing osteoblast differentiation is added. Thus, there is an economical advantage. The supplementary factors inducing osteoblast differentiation may be BMP-4, vitamin C (ascorbic acid, AA), β-glycerophosphate (BGP), umbilical blood serum, tauroursodeoxycholic acid, dexamethasone, L-alanyl-L-glutamine, glycerol 2-phosphate, and a combination thereof.

In the present disclosure, the culture scaffold is characterized in that osteoblast differentiation occurs well under inflammatory conditions, that is, under the condition where inflammatory factors exist. That is, the differentiation may be performed under inflammatory conditions. The inflammatory factors may be, but is not limited to, a cytokine or an endotoxin (LPS, lipopolysaccharide), including TNF (tumor necrosis factor)-α, IL (interleukin)-1β.

In the present disclosure, the culture scaffold is characterized by suppressing the generation of reactive oxygen species (ROS). Accordingly, the culture scaffold of the present disclosure is characterized in that the differentiation of osteoblasts is enhanced by suppressing active oxygen generated by an inflammatory environment caused by differentiation of cells.

In the present disclosure, the culture scaffold is not greatly affected by the density of cells. However, when used as a culture scaffold, the cell density for inducing the optimal differentiation may be $1 \times 10^2$ to $1 \times 10^5$ cells/well, more preferably $3 \times 10^3$ to $3 \times 10^4$ cells/well, which is based on 24 wells, and can be sufficiently varied depending on the size of wells. The present disclosure is not limited to the above numerical values.

In the present disclosure, the term "kit" may further include various constituents such as one or more types of solutions or devices suitable for the differentiation of stem cells or precursor cells in addition to a culture scaffold of the present disclosure so that stem cells can be differentiated into osteoblasts more efficiently. The constituents included by the above addition are not particularly limited as long as they can affect the differentiation into osteoblasts, but may be used alone or in a combination of a medium for stem cell culture, a stem cell differentiation inducing substance, a culture container, an endothelial cell for stem cell co-culture.

As another example, the present disclosure provides a method for differentiating stem cells or precursor cells into osteoblasts, in which the method includes: (a) inoculating and culturing stem cells or precursor cells in the culture scaffold; and (b) differentiating the cultured stem cells or precursor cells into osteoblasts.

In the present disclosure, the "differentiation" of the step (b) may be induced using a small amount of supplementary factors inducing osteoblast differentiation or a medium for inducing osteoblast differentiation. The medium may be a medium for inducing differentiation commonly used in the pertinent technical field.

As another example, the present disclosure provides a method for preparing a culture scaffold for promoting osteoblast differentiation from stem cells or precursor cells, in which the method includes: (a) preparing a mold composed of a ridge and a groove; (b) preparing a negative mold from the mold; and (c) preparing a polymer, which is a culture scaffold, from the negative mold.

In the present disclosure, the preparation method may further include: treating the culture scaffold with ultraviolet ozone (UVO); or treating the culture scaffold with the one selected from a group consisting of titanium (Ti), aluminum (Ai), vanadium (V), titanium alloy (Ti-6Ai-4V), stainless steel (316L), cobalt alloy (Co—Cr—Mo) and nickel-titanium alloy (NiTi) on the culture scaffold.

In the present disclosure, the mold is also referred to as a mold, and is a solid substance having a certain shape and is a substance used for preparing the culture scaffold of the present disclosure.

The polymer of the step (c) may be TPT, TDP, TGD, TAC, TPTM, PCL, collagen, gelatin, hyaluronic acid, keto acid, laminin, keratin, alginate, fibronetin, polyglycolic acid, poly lactic acid, polylactic acid-glycolic acid copolymer, polyamino acid, polyanhydride, polyorthoester or polyurethane, and any polymer that can be used in vivo can be used without limitation.

In addition, the polymer of the step (c) may be a substance further including a photoinitiator, in which a mixing ratio of the polymer and the photoinitiator is 95:5 (v/v), but is not limited thereto. In addition, the photoinitiator may be 2'-hydroxy-2-methyl-propiophenone (HOPP), 2,2'-diethoxyacetophenone, 2,2'-dibutoxyacetophenone, p-t-butyltrichloroacetophenone, p-t-butyldichloroacetophenone, 4-chloroacetophenone, 2,2'-dichloro-4-phenoxyacetophenone, benzophenone, 4,4'-dimethylaminobenzophenone, 4,4'-dichlorobenzophenone, 3,3'-dimethyl-2-methoxybenzophenone, 4-phenyl benzophenone, hydroxy benzophenone, acrylated benzophenone, 4,4'-bis(dimethyl amino) benzophenone, 4,4'-bis(diethyl amino) benzophenone, thioxanthone, 2-chloro thioxanthone, 2-methylthioxanthone, isopropyl thioxanthone, 1-[9-ethyl-6-(2-methylbenzoyl)-9H-carbazol-3-3-yl]-1-(O-acetyloxime), 2,4-diethyl thioxanthone, 2,4-diisopropyl thioxanthone, 2-chloro thioxanthone, benzoin, benzoin methyl ether, benzoin ethylether, benzoin isopropylether, benzoin isobutylether, benzyldimethylketal, 4,6-trichloro-s-triazine, 2-phenyl-4,6-bis(trichloromethyl)-s-triazine, bis (trichloromethyl)-6-styryl-s-triazine, 2-4-trichloro methyl (piperonyl)-6-triazine, 2-4-trichloromethyl(4'-methoxystyryl)-6-triazine, 2-(3',4'-dimethoxy styryl)-4,6-bis(trichloro methyl)-s-triazine, 2-(4'-methoxy naphthyl)-4,6-bis(trichloromethyl)-s-triazine, 2-(p-methoxyphenyl)-4,6-bis(trichloromethyl)-s-triazine or 2-biphenyl-4,6-bis(trichloromethyl)-s-triazine, and preferably HOPP, but is not limited thereto.

The redundant contents are omitted in consideration of the complexity of the present specification, and the terms not otherwise defined in the present specification have the meanings commonly used in the technical field to which the present disclosure pertains.

Hereinafter, as an aid to understanding, the present disclosure will be described in detail with reference to the examples. It should be understood, however, that the following examples are for illustrative purposes only and are not intended to limit the scope of the present disclosure. Examples of the present disclosure are provided to more fully explain the present disclosure to a person having average knowledge in the pertinent art.

EXAMPLE 1

Preparation and Confirmation of a Scaffold Having a Ridge and Groove Pattern 1-1. Preparation of a Scaffold Having a Ridge and Groove Pattern and Confirmation of Surface Shape
1-1-1. Preparation First, a silicon master mold was prepared through standard photolithography and dry etching. In addition to this, a poly (dimethylsiloxane) (PDMS) solution (Sigma-Aldrich, St. Louis, Mo., USA) was prepared by mixing a silicone elastomer base and a silicon elastomer curing agent in a ratio of 10:1 (w/w), which was then placed in the silicon master mold and degassed. The PDMS solution was then cured at 80° C. for 4 hours. The cured PDMS molds were stripped from the master mold using the low surface force and elasticity of the PDMS.

Subsequently, in order to prepare a patterned scaffold in a cell culture plate, TPT (Mn=~644) (Sigma-Aldrich) and photoinitiator HOPP (97%, Sigma-Aldrich) were mixed in a ratio of 95:5 (v/v) to prepare a TPT precursor solution, which was added to a cell culture plate, and PDMS mold was covered thereon. Thereafter, the TPT precursor solution was cured for 90 minutes at a wavelength of 365 nm and UV light of 135 mW/cm$^2$ (Fusion cure system, Minuta Technology, Republic of Korea). From the TPT having a cured ridge and groove pattern, the PDMS mold was separated. An additional curing process was then carried out using UV on the TPT patterned for 90 minutes to minimize residual TPT oligomers and the UVO of the ozone curing system was treated to the patterned structure for 1 hour to increase the physical properties of the surface. Thereafter, all the patterned TPTs, i.e., the scaffold sample, were sterilized. The series of processes are illustrated schematically in FIG. 1.

1-1-2. Confirmation of Surface Shape of a Scaffold Having a Ridge and Groove Pattern The pattern images in the scaffold prepared in Example 1-1-1 were analyzed by a field emission scanning electron microscope (FE-SEM, S-4800, Hitachi, Tokyo, Japan). In addition, in order to further verify the shape of the pattern, the scaffold sample was sputter-coated and imaged at an accelerating voltage of 5 kV using FE-SEM. The results are illustrated in FIG. 2.

Figure 2:
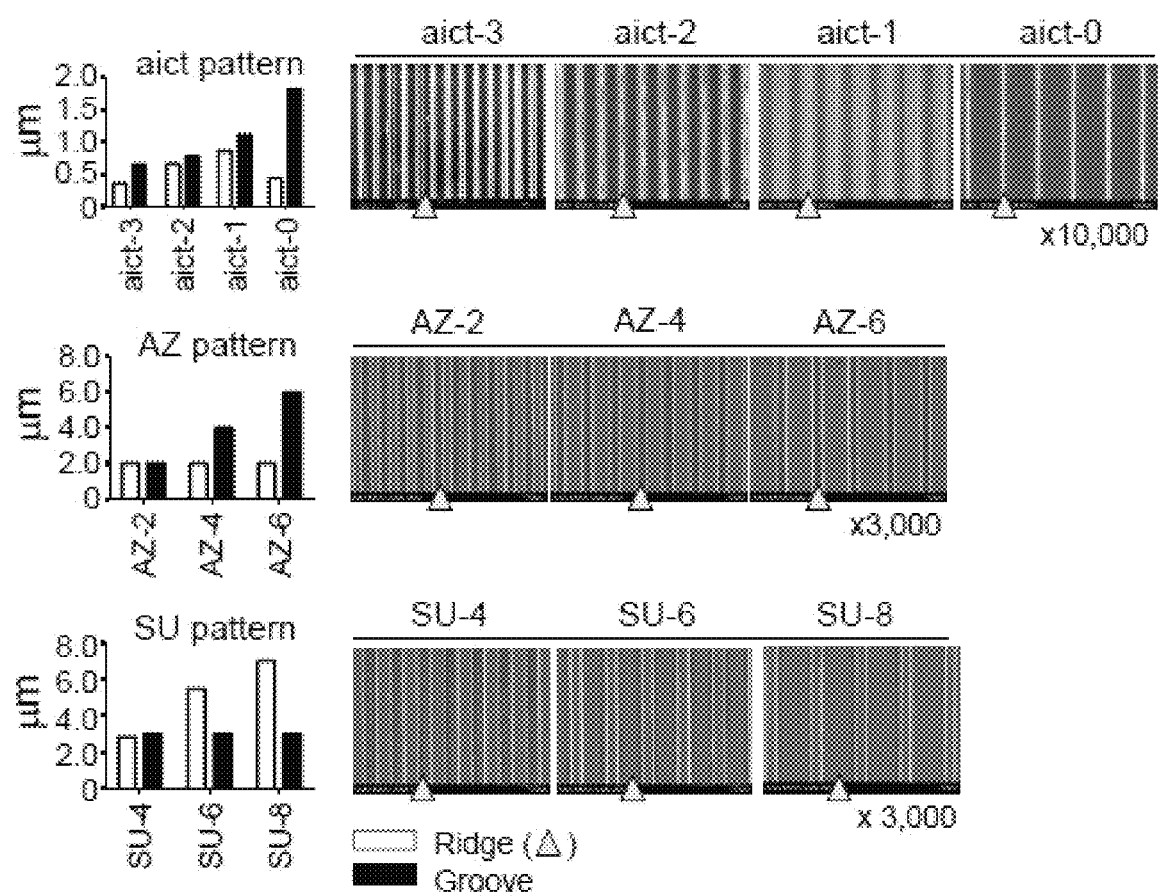
FIG. 2 represents graphs illustrating the shape of a scaffold having a ridge and groove pattern using a scanning electron microscope (SEM).

As illustrated in FIG. 2, the scaffold prepared through Example 1-1-1 has two micro-sized patterns (AZ pattern or SU pattern) and a sub-micro-sized pattern having fixed ridge or a groove. That is, it was confirmed to have a groove pattern of various combinations as shown in Table 1 below having a ridge width of 0.35 to 7 μm and a groove width of 0.65 to 6 μm.

TABLE 1

|  |  | Width of ridge (μm) | Width of groove (μm) |
|---|---|---|---|
| Control group | Flat scaffold | 0 | 0 |
| Experimental group | aict-3 | 0.35 | 0.65 |
|  | aict-2 | 0.65 | 0.76 |
|  | aict-1 | 0.85 | 1.1 |
|  | aict-0 | 0.5 | 1.8 |
|  | AZ-2 | 2 | 2 |
|  | AZ-4 | 2 | 4 |
|  | AZ-6 | 2 | 6 |
|  | SU-4 | 2.83 | 3 |
|  | SU-6 | 5.47 | 3 |
|  | SU-8 | 7 | 3 |

In addition, a contact angle (CA) of the boundary formed when the liquid contacts with a groove pattern on the scaffold of the present disclosure using deionized water was measured with a Phenix 150 surface angle analyzer (Surface Electro Optics, Suwon, Republic of Korea) and analyzed with Image XP 5.9 software. The results are illustrated in FIG. 3A, and the graphs thereof are illustrated in FIG. 3B.

Figure 3A:
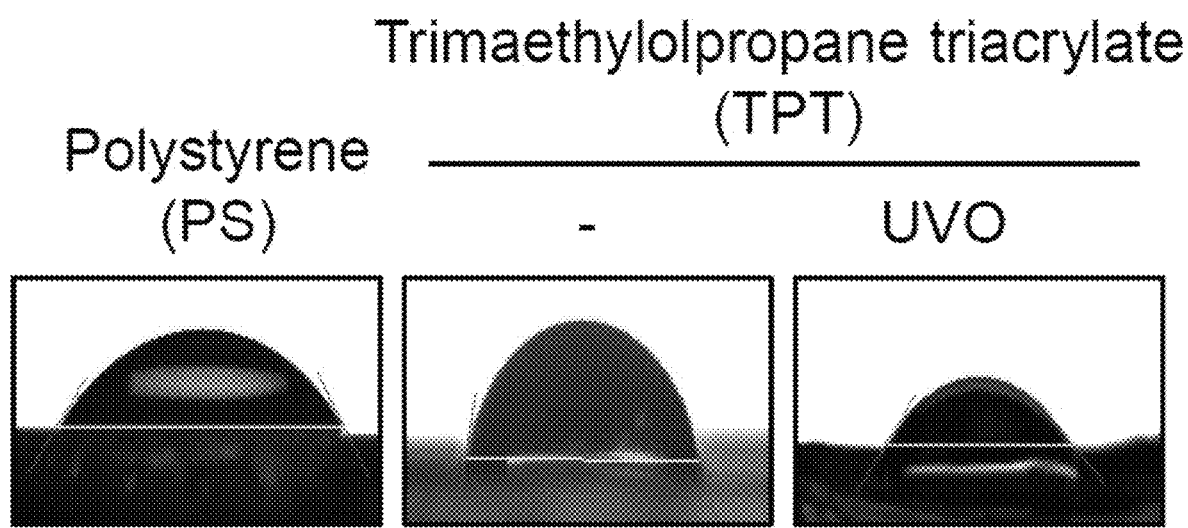
FIG. 3A represents a diagram illustrating a contact angle of the boundary between the scaffold having a ridge and groove pattern using a surface angle analyzer.
Figure 3B:
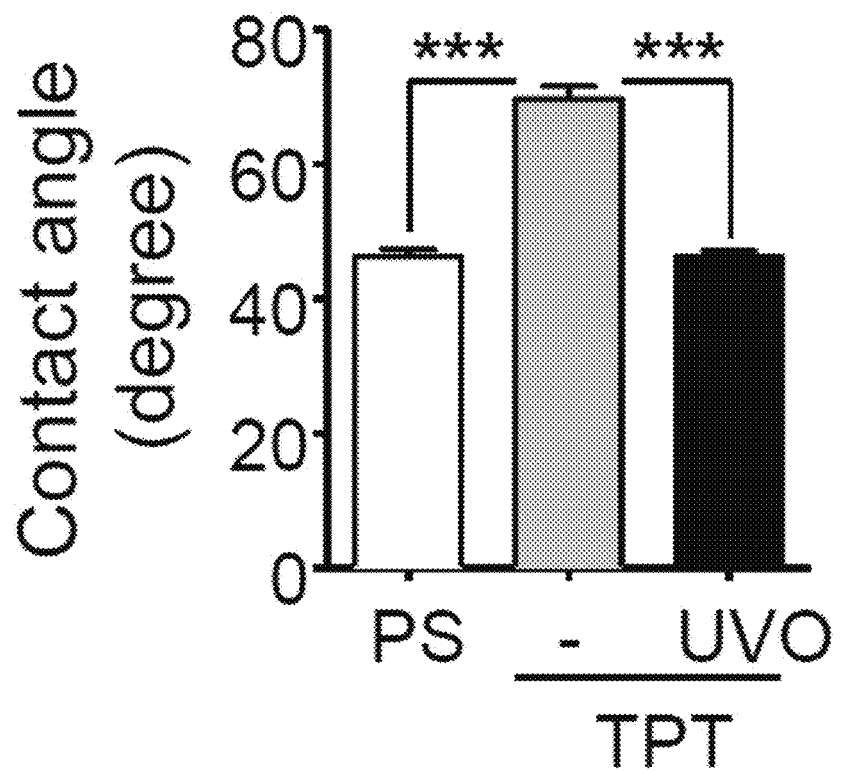
FIG. 3B represents a bar graph illustrating the results shown in FIG. 3A.

As illustrated in FIGS. 3A and 3B, it was confirmed that the contact angle with respect to polystyrene (PS) used mainly in a general culture dish was about 45°, the contact angle before UVO treatment was about 70°, and the same contact angle with PS was obtained after UVO treatment. In addition, in this example, it was confirmed that there was no change in the contact angle for 6 days after UVO treatment, and that no additional physical property change over time was generated due to treatment with UVO.

Figure 4:
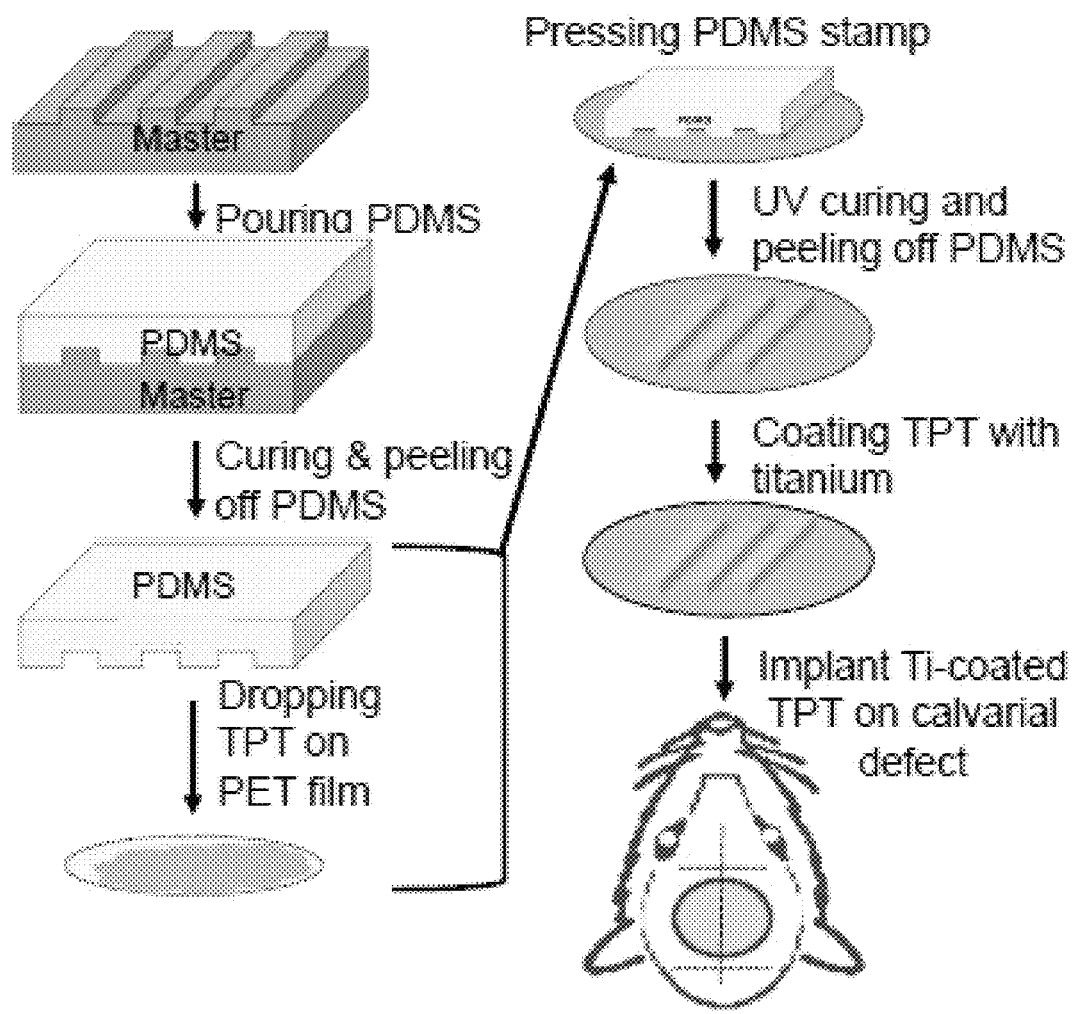
FIG. 4 represents a diagram schematizing a method for preparing a scaffold having a ridge and groove pattern coated with titanium dioxide (Ti).

1-2. Preparation of a Scaffold Having a Ridge and Groove Pattern Coated with a Titanium Dioxide (Ti) and Confirmation of Cytotoxicity 1-2-1. Preparation A scaffold having a ridge and groove pattern was prepared in the same manner as in Example 1-1-1 except that TPT was added to a polyethylene terephthalate (PET) film (Kolon Industries, Gwacheon, Republic of Korea), instead of being added to a cell culture plate. Thereafter, a Ti film of 50 nm or less was sputtered on the TPT as a patterned scaffold using a DC Marktron sputter system (KVS-2004L; Vacuum Tech, Gimpo, Republic of Korea). Then, the distance between the Ti target and the substrate was set to 15 cm, the basic pressure in the sputter chamber was set to $10^{-6}$ Torr, and a 99.99% Ti target (RND Korea, Gwangmyeong, Republic of Korea) was used. Then, with the plasma for sputtering for 10 minutes, Ar (argon) gas with a direct current (DC) of 100 W, a flow rate of 15 sccm and a pressure of $2 \times 10^{-3}$ Torr was produced. In order to carry out in vivo animal experiments, a scaffold having a Ti-coated groove pattern was cut into a disc-shaped structure (12 mm in diameter). This is a step for evaluating in vivo bone remodeling. The above series of processes are illustrated schematically in FIG. 4.

1-2-2. Confirmation of Cytotoxicity

In order to measure the extracellular cytotoxicity of the scaffold with the Ti-coated ridge and groove pattern, the scaffold sample prepared in Example 1-2-1 was treated on a 24-well culture plate, and then MC3T3 cells were dispensed at a concentration of $3 \times 10^4$ cells/well. After 24 hours of culturing, cell viability was measured by CCK-8 assay kit (Sigma-Aldrich) according to the manufacturer's manual. The results are illustrated in FIG. 5.

Figure 5:
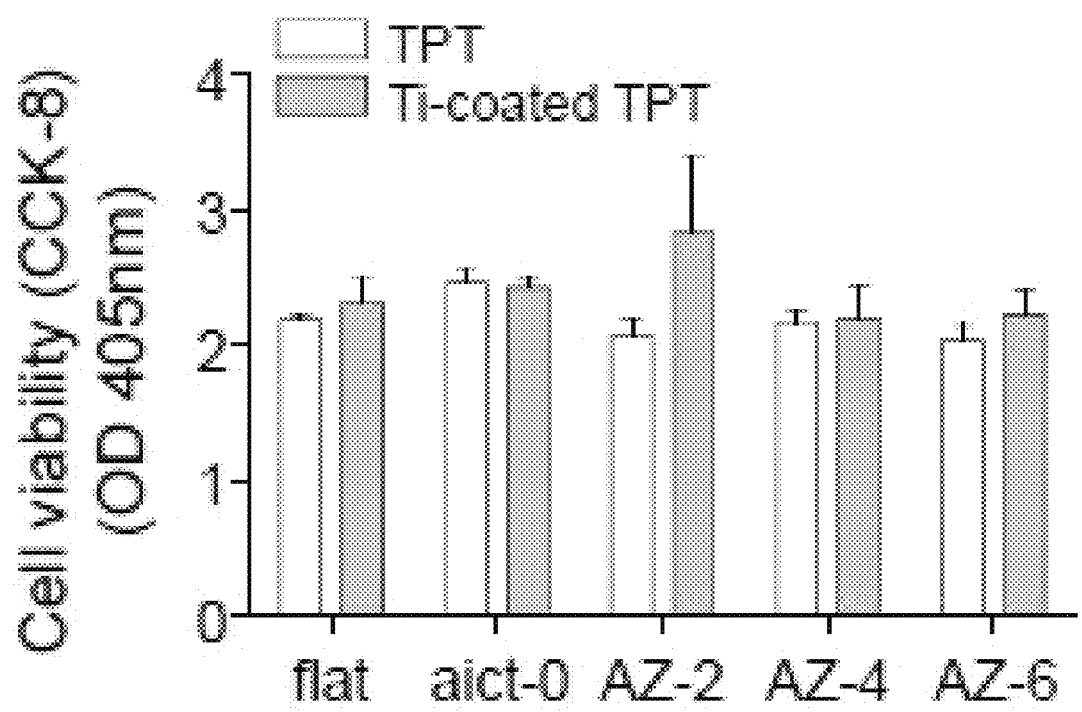
FIG. 5 represents a bar graph illustrating the cytotoxicity of a scaffold having a ridge and a groove pattern coated with titanium dioxide.

As illustrated in FIG. 5, it was confirmed that even when the scaffold having a pattern was coated with Ti, it did not have cytotoxicity to MC3T3 cells in vitro. This indicates that a scaffold having a Ti-coated pattern of the present disclosure can be used in vivo.

EXPERIMENTAL EXAMPLE 1

Differentiation into Osteoblasts by a Scaffold Having a Ridge and Grove Pattern of the Present Disclosure 1-1. Securing and Culturing Precursor Cells or Stem Cells of Osteoblasts MC3T3 cells (hereinafter, referred to as 'MC3T3'), which are precursor cells of osteoblasts, were purchased from the American Type Culture Collection (ATCC, Manassas, Va., USA), and cultured in a α-MEM medium supplemented with 10% fetal bovine serum without AA, 1% penicillin/streptomycin and 1% glutamine (Life Technologies, Carlsbad, Calif., USA).

Adipose tissue-derived mesenchymal stem cells (Ad-MSCs) were obtained from human adipose tissue, and cultured in a medium mixed at a ratio of 4:1 of endothelial growth medium (EGM, Lonza, Basel, Switzerland) and DMEM (Life Technologies) as a conditioned medium.

In addition, the ligament was separated from the surface of the extracted tooth, and then the periodontal ligament stem cells (PDLSC) were separated after reaction under the condition of 37° C. for 1 hour in a solution of 3 mg/mL of collagenase type I (Sigma-Aldrich) and 4 mg/mL of dispase (Sigma-Aldrich).

Thereafter, each cell was added to a culture plate containing a serum-supplemented medium and cultured for two days to allow cells to adhere well to the plate. Then, the cells used a scaffold having a ridge and groove pattern prepared in Example 1-1-1, a TPT scaffold, which is a control group (flat), and a PS scaffold, which is generally used as a scaffold for cell culture, and dispensed at an approximately filled concentration ($3 \times 10^4$ cells/well) on the bottom.

In the following experiments, Ad-MSC and PDLSC cells were used in 2 to 4 passages, and the study protocols were approved by the Institutional Review Board of Seoul National University Hospital (#C-1401-121-550)

1.2. Differentiation into Osteoblasts According to the Addition of Osteogenic Factors In order to induce the differentiation of each cell into osteoblasts, the experiment was carried out in the same manner as in the Experimental Example 1-1 except that additional osteogenic factors containing AA (100 μg/mL or 50 μg/mL, Sigma-Aldrich) and BGP (10 mM or 5 mM, Sigma-Aldrich) were added.

At that time, as to the osteogenic factors, the experiments were performed for each of the experimental group that treats a full-dose of 100 μg/mL AA and the experimental group that treats a half-dose of the optimal dose of 50 μg/mL AA and 5 mM BGP.

1-3. Differentiation into Osteoblasts Induced by Different Cell Densities

In order to confirm the difference in osteoblast differentiation effect of the scaffold of the present disclosure according to the change in cell densities, experiments were carried out in the same manner as in Experimental Example 1-1, differing only in cell densities used. At this time, the cell density was $3 \times 10^4$, $3.75 \times 10^3$, $1.87 \times 10^3$, $0.93 \times 10^3$ and $0.46 \times 10^3$ cells per well for experiments.

1-4. Differentiation into Osteoblasts According to the Addition of Inflammatory Factors In order to confirm the difference in osteoblast differentiation effect of the scaffold of the present disclosure produced by inflammatory factors, experiments were carried out in the same manner as in Experimental Example 1-1, except that LPS-stimulated splenocytes in the cell medium, cytokine TNF-α (10 ng/mL, PeproTech, Rocky Hill, N.J., USA) or IL-1β (10 ng/mL, PeproTech) were treated.

At this time, splenocytes separated from C57BL/6J mice (Joongang Laboratory Animal Co., Seoul, Republic of Korea) were stimulated with LPS (1 μg/mL) for 24 hours at 37° C. under the condition of 5% $CO_2$, and then separated thereafter. The separated culture solution was centrifuged at 500×g for 5 minutes, and then the one that separates only the supernatant was used. The LPS-stimulated splenocytes were referred to as a culture solution.

EXPERIMENTAL EXAMPLE 2

Differentiation into Osteoblasts by a Scaffold Having a Ridge and Groove Pattern of the Present Disclosure and Confirmation of Feature 2-1. Confirmation of Osteoblast Differentiation by Mineralization Assay
2-1-1. Confirmation of Osteoblast Differentiation When the MC3T3, Ad-MSCs and PDLSCs were differentiated into osteoblasts and cultured on the $10^{th}$, $20^{th}$ and $8^{th}$ days, respectively, in the manner described in Experimental Example 1-1, the differentiation results were analyzed by Alizarin Red S (Sigma-Aldrich) staining. In other words, the degree of differentiation into osteoblasts was confirmed by confirming the accumulation of intracellular calcium in osteoblasts through Alizarin Red S staining.

Figure 6A:
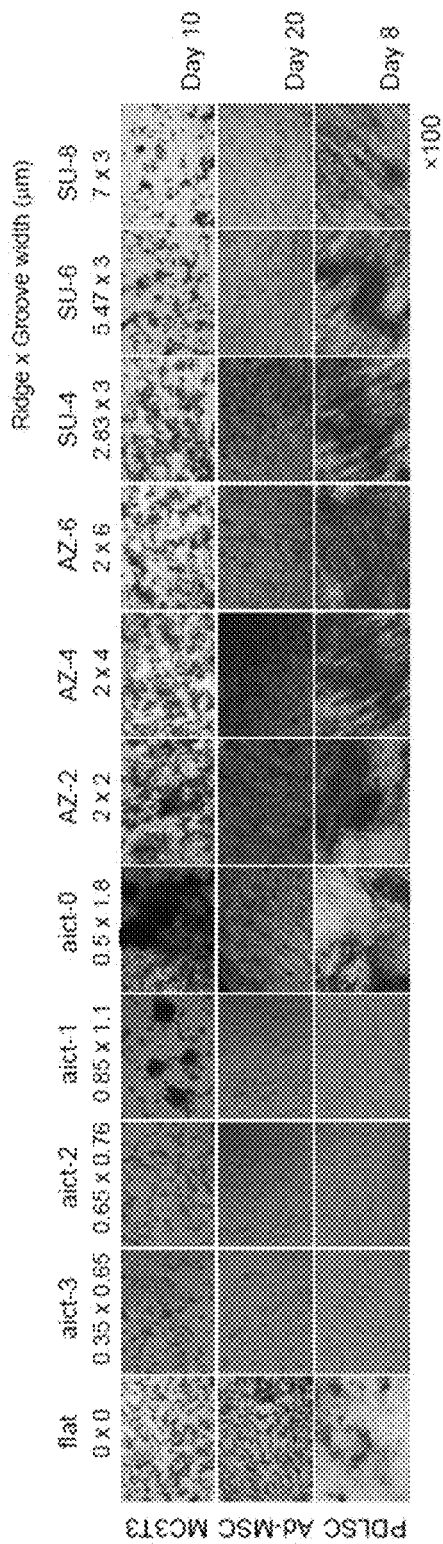
FIG. 6A represents photographs illustrating the effect of inducing osteoblast differentiation of a scaffold having a ridge and groove pattern through mineralization analysis.

Specifically, each cell cultured through Experimental Example 1-1 was washed with phosphate-buffered saline (PBS) and fixed with 10% formaldehyde at a room temperature for 15 minutes. After washing them twice with distilled water, it was reacted with 40 nM Alizarin Red S (pH 4.1) for 20 minutes to confirm that the calcium formed in osteoblasts was stained red. Images were obtained with an optical microscope (Olympus, Tokyo, Japan), which is illustrated in FIG. 6A. In addition, quantitative analysis of the images was standardized through the area of the cell layer using Image J (NIH, http://imagej.nih.gov/ij/National Institute of Health, Bethesda, Md., USA), and the quantification of calcium accumulation in the cell layer (Alizarin Red S value, arbitrary unit) was performed. The results are illustrated in FIG. 6B.

In addition, the approximate Alizarin Red S value was measured to confirm whether the degree of differentiation of MC3T3, Ad-MSC and PDLSC varied according to various groove patterns of the scaffold of the present disclosure. To this end, with a generic cubic polynomial having two variables, the interpolation of the substances for a flat or eight groove patterns (aict-2, aict-1, aict-0, AZ-2, AZ-4, SU-4, SU-6 and SU-8) was calculated. Accordingly, a polynomial was derived from a linear equation system obtained by substituting the data into a generic cubic polynomial. In order to find an effective groove pattern, it has been confirmed that the interpolation of a polynomial has a rectangular subdomain with respect to a ridge-groove range having a reasonably large minimum value. The results are illustrated in FIG. 6C.

Figure 6B:
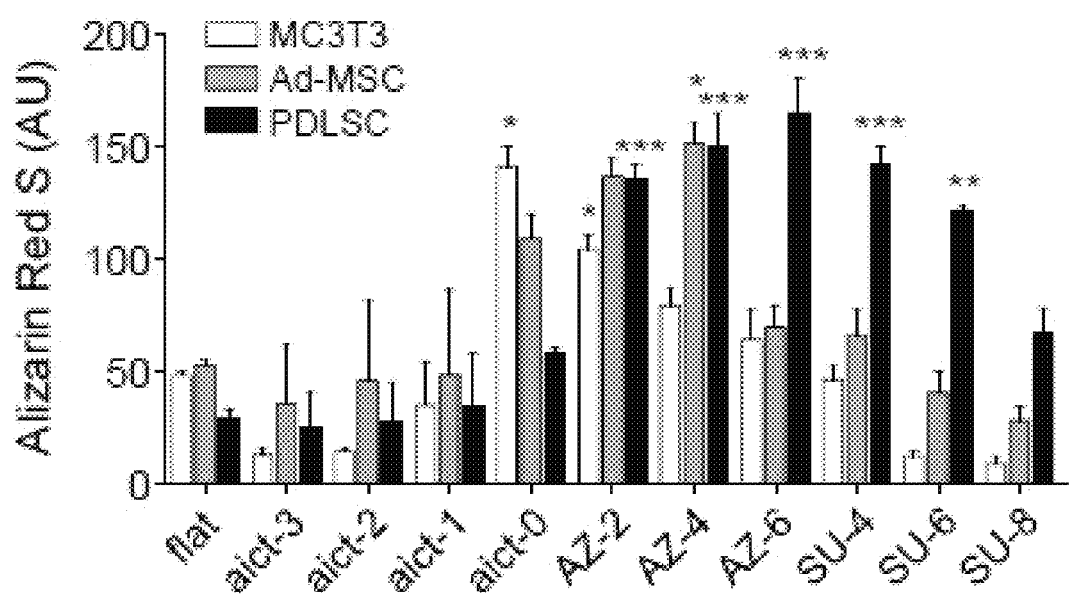
FIG. 6B represents a bar graph illustrating the result of FIG. 6A.
Figure 6C:
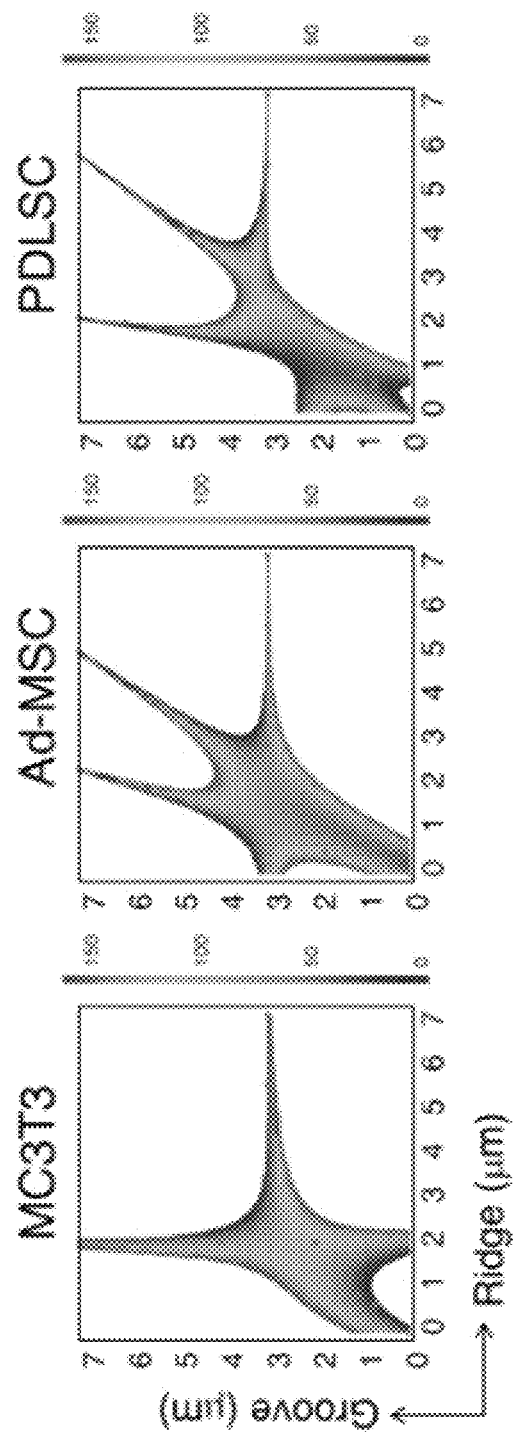
FIG. 6C represents graphs shown as heat maps estimating the ridge-groove range suitable for osteoblast differentiation in each cell by using a third-degree polynomial function of the values shown in the above FIG. 6B.

As illustrated in FIGS. 6a and 6b, it can be confirmed that MC3T3, Ad-MSC and PDLSC are well differentiated into osteoblasts in each groove pattern, and particularly, it was confirmed that the osteoblast differentiation was particularly active in the scaffold patterned with aict-0, AZ-2, AZ-4, AZ-6, SU-4, and SU-6.

Specifically, MC3T3 showed excellent osteoblast differentiation potency on a scaffold having a pattern ridge width of 0.5 to 2.83 μm and a groove width of 1.1 to 6 μm as compared with the flat scaffold, which is a control group. It was confirmed that the maximum potency of osteoblast differentiation is shown in a scaffold having a ridge of 0.5 to 2 μm and a groove of 1.8 to 4 μm.

In addition, it was confirmed that Ad-MSC has excellent osteoblast differentiation potency on a scaffold having a pattern ridge width of 0.5 to 2.83 μm and a groove width of 1.1 to 6 μm as compared with the flat scaffold, which is a control group. It was confirmed that the maximum potency of osteoblast differentiation has a ridge of 0.5 to 2 μm and a groove of 1.8 to 4 μm.

In addition, it was confirmed that the PDLSC has excellent osteoblast differentiation potency on a scaffold having a pattern ridge width of 1 to 4 μm and a groove width of 2 to 6 μm as compared with the flat scaffold, which is a control group. It was confirmed that the maximum potency of osteoblast differentiation has a ridge of 2 to 2.83 μm and a groove of 2 to 6 μm.

To sum up, as shown in FIG. 6C, which interpolates the above values, the following Mathematical Equations 1 to 3, which can measure the optimal ridge-groove range for osteoblast differentiation of each cell, were derived. Each equation is the values for MC3T3, Ad-MSC, and PDLSC. At this time, the value of f(x, y) is the result value of osteoclast formation, x is the width of a ridge, and y is the width of a groove.

$$f_{MC3T3}(x, y) = 48 - 282.3743010506538x + 150.0643654964519x^2 - 2.1578366571518117x^3 + 106.00507418528939y + 47.057707899876796xy - 38.1698690150136x^2y + 5.799343765475734y^2 - 5.725807288851501xy^2 + 1.5469548619315638y^3$$

[Mathematical Equation 1]

-continued $$f_{Ad-MSC}(x, y) = 52.5 - 186.0249972891292x + \\ 420.1686722594631x^2 + \\ 0.23413346166748633x^3 + \\ 113.62075782914779y - \\ 347.796009555016xy - \\ 141.0900051731596x^2y + \\ 48.29374156278727y^2 + \\ 136.97784948772315xy^2 - \\ 27.854120044852811y^3$$ [Mathematical Equation 2]

$$f_{PDLSC}(x, y) = 29 - 276.24302367019254x + \\ 374.7159612153953x^2 + \\ 2.890595500378056 6x^3 + \\ 205.73031785654726y - \\ 217.53411649652557xy - \\ 141.83277489850784x^2y - \\ 44.936421391088395y^2 + \\ 131.99978088607176xy^2 - \\ 1823963669842127y^3.$$ [Mathematical Equation 3]

2-1-2. Confirmation of the Effect of Osteogenic Factors

Figure 7A:
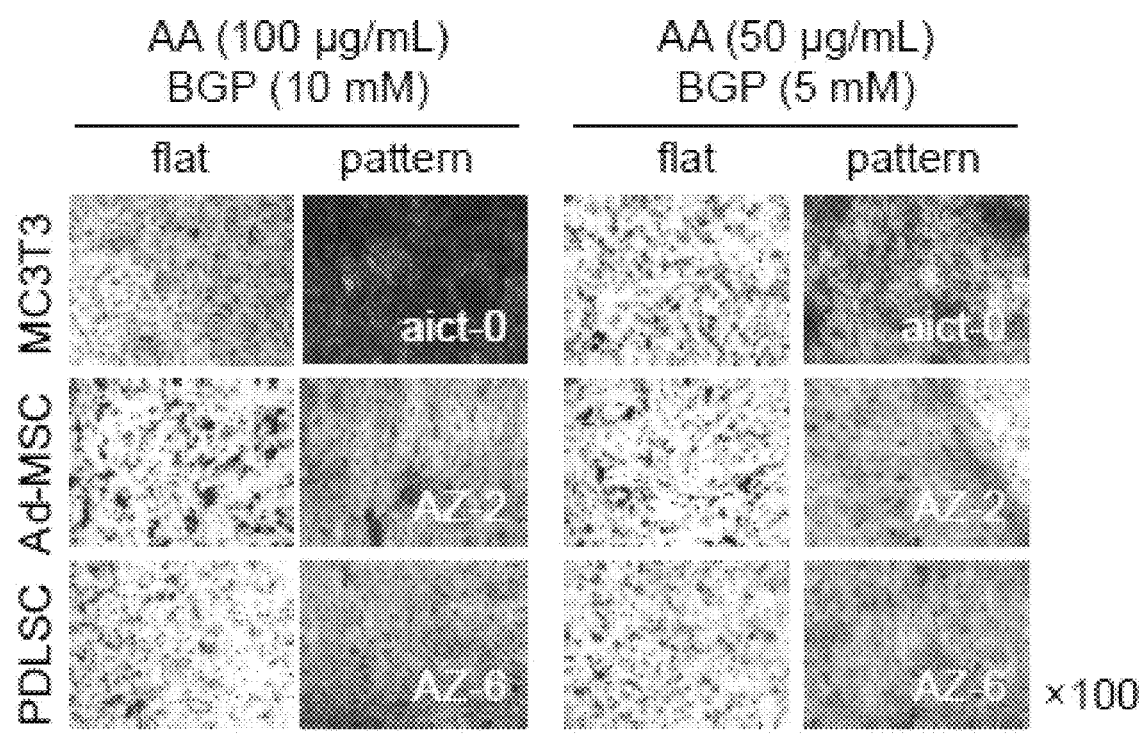
FIG. 7A represents photographs illustrating the effect of osteogenic factors in inducing osteoblast differentiation on a scaffold having a ridge and groove pattern through mineralization analysis.
Figure 7B:
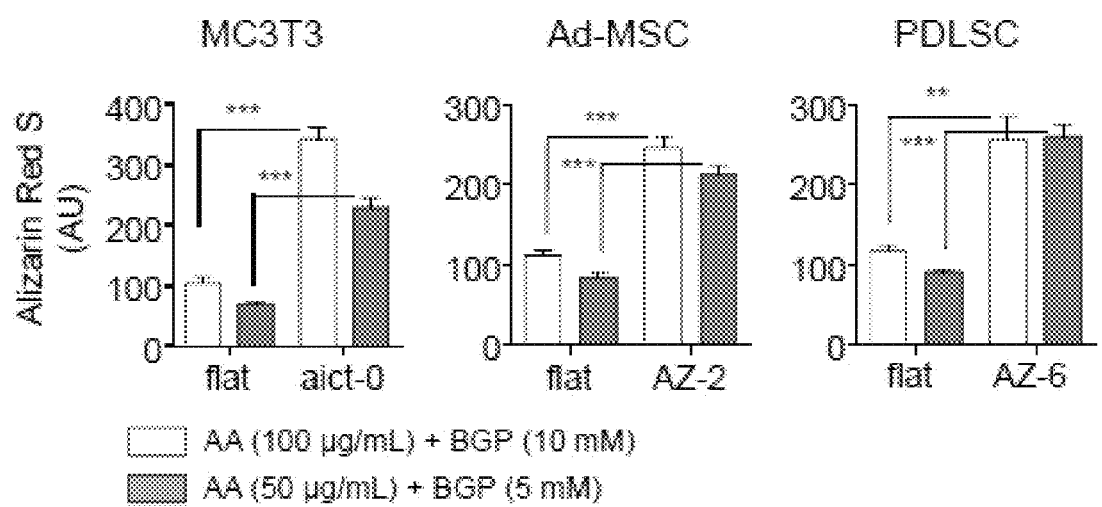
FIG. 7B represents bar graphs illustrating the result of FIG. 7A.

In the osteoblast differentiation by the scaffold having a ridge and groove pattern of the present disclosure, in order to confirm the effect of the osteogenic factors known to be essential for the conventional osteoblast differentiation, the degree of differentiation of each cell that induces the osteoblast differentiation by the method of Experimental Example 1-2 was confirmed. The cells were then analyzed by Image J following Alizarin Red S staining, as described in Experimental Example 2-1-1. The results were calculated by interpolation. The results are illustrated in FIGS. 7A and 7B.

As illustrated in FIG. 7, it was confirmed that even when the treatment concentration of AA and BGP was reduced, there was no significant difference in the potency of osteoblast differentiation of the scaffold having the pattern. This shows that the physical properties of the ridge and groove patterns themselves provide the environment necessary for osteoblast differentiation.

2-1-3. Confirmation of the Effect of Cell Density

Figure 8A:
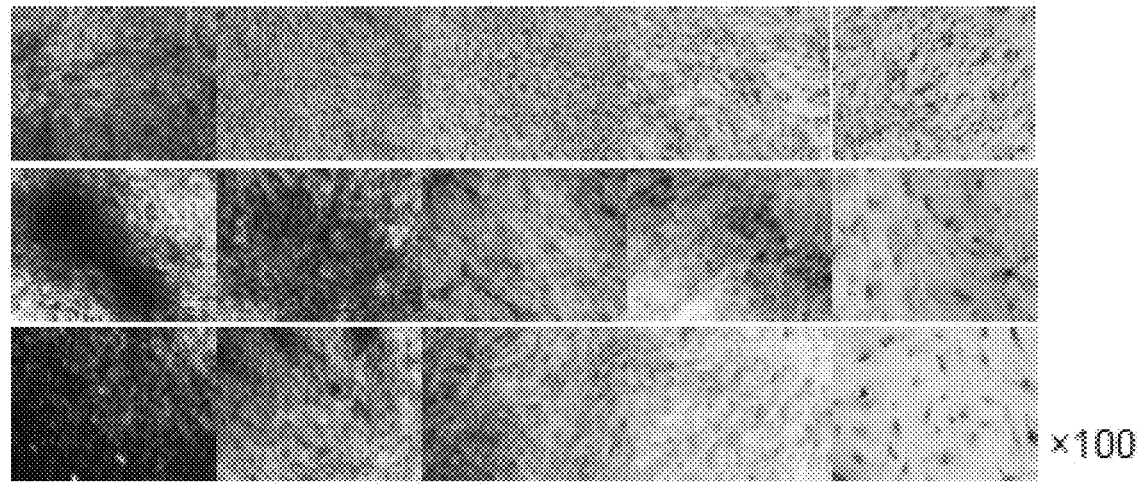
FIG. 8A represents photographs illustrating the effect of cell density during a process of osteoblast differentiation on a flat scaffold (PS, flat) having a ridge and groove pattern through mineralization analysis.
Figure 8B:
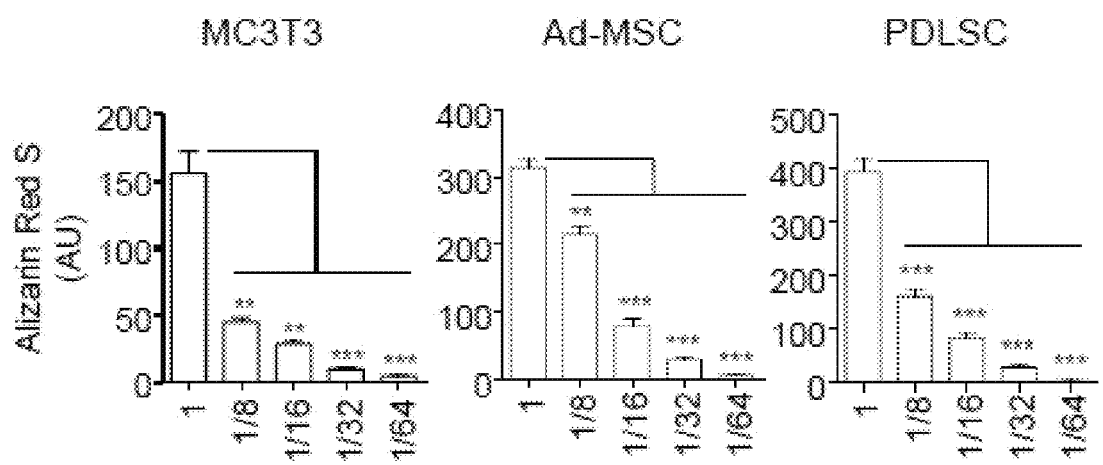
FIG. 8B represents bar graphs illustrating the performance results on a flat scaffold (PS, flat).
Figure 8C:
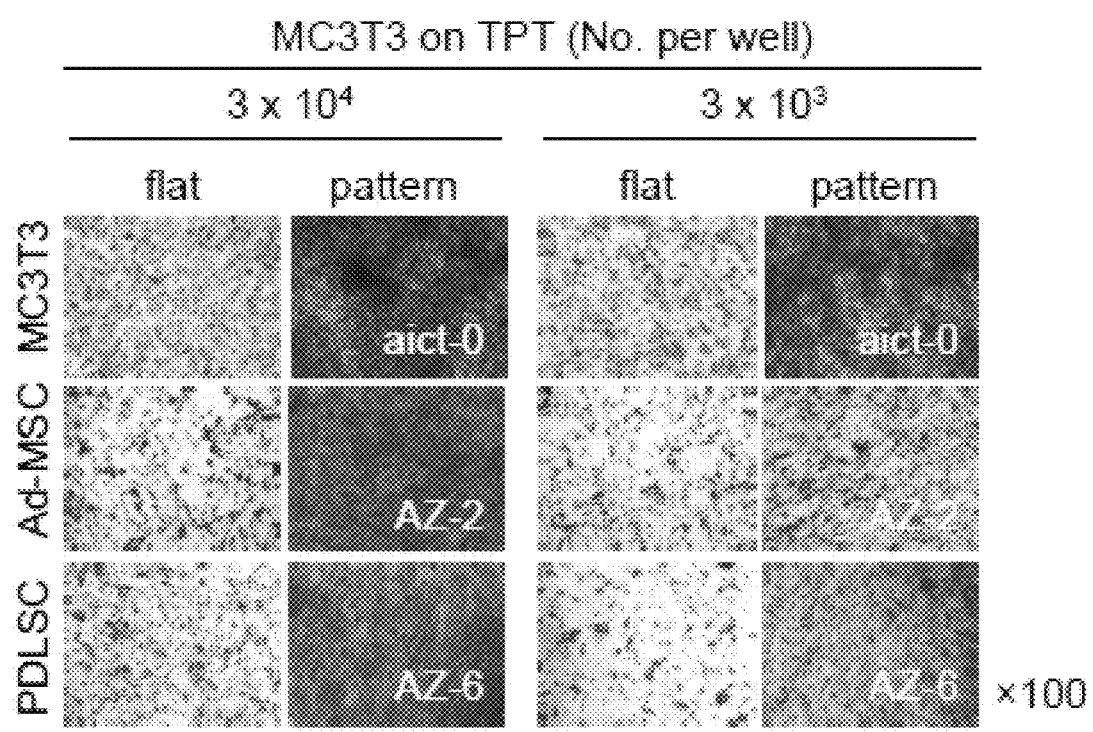
FIG. 8C represents photographs illustrating performance results on a scaffold (TPT; aict-0, AZ-2, AZ-6) having a ridge and groove pattern.
Figure 8D:
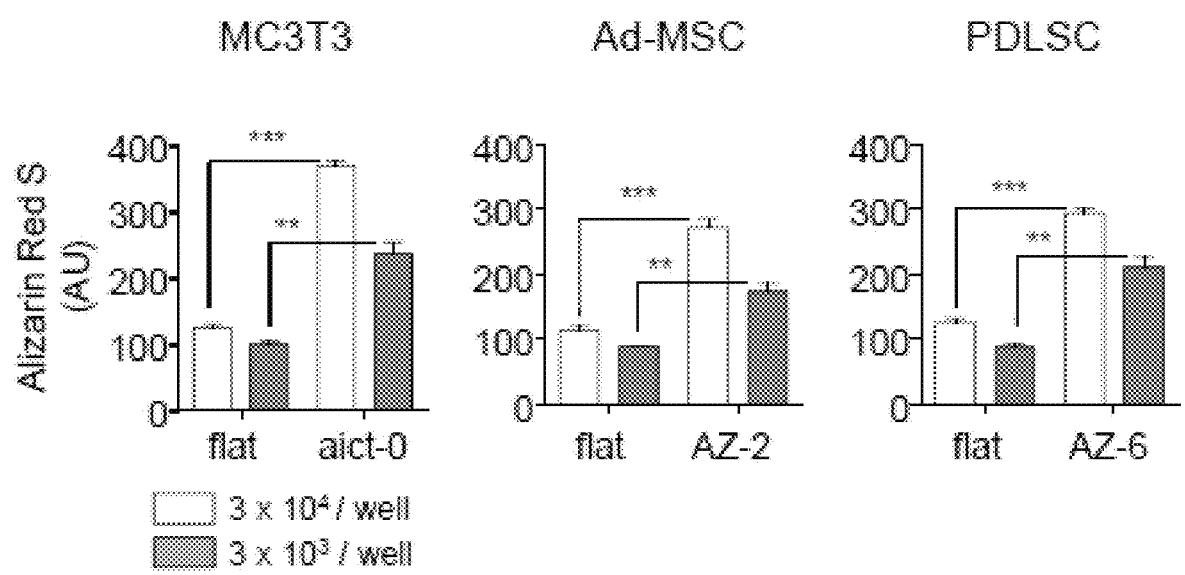
FIG. 8D represents bar graphs illustrating the performance results on a scaffold (TPT; aict-0, AZ-2, AZ-6) having a ridge and groove pattern.

In the differentiation into osteoblasts by the scaffold having a ridge and groove pattern of the present disclosure, in order to confirm the effect of cell density, the degree of differentiation of each cell that induces the osteoblast differentiation by the method of Experimental Example 1-2 was confirmed. The cells were then analyzed by Image J following Alizarin Red S staining, as described in Experimental Example 2-1-1. The results were calculated by interpolation. The results of performing the flat scaffold (PS, flat) are shown in FIGS. 8A and 8B. The results of performing the scaffolds having a ridge and groove pattern of the present disclosure (TPT; aict-0, AZ-2, AZ-6) are illustrated in FIGS. 8C and 8D.

As illustrated in FIG. 8, it was confirmed that the degree of osteoblast differentiation was remarkably decreased as the cell density decreased in the flat scaffold (FIGS. 8A and 8B). However, it was confirmed that the scaffold having the groove pattern of the present disclosure well maintain the osteoblast differentiation even at $3\times10^3$ cells/well, which is $\frac{1}{10}$ density of the appropriate cell density of $3\times10^4$ cells/well (FIGS. 8C and 8D). This shows that the physical characteristics of the groove pattern serve to overcome environmental limitations by providing the necessary environment for osteoblast differentiation.

2-1-4. Confirmation of the Influence of Inflammatory Factors

Figure 9A:
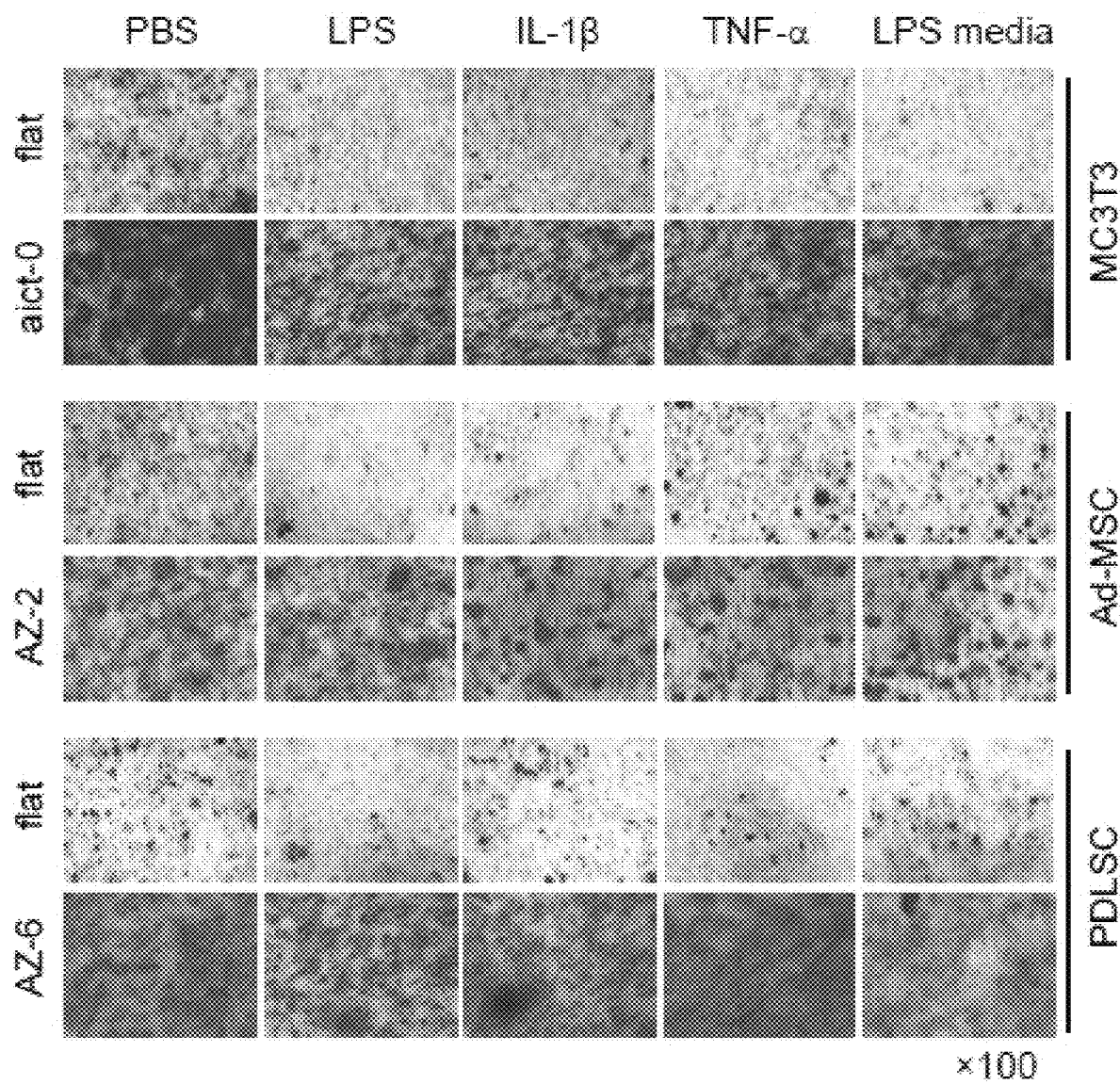
FIG. 9A represents photographs illustrating the effect of inflammatory factors during a process of osteoblast differentiation on a scaffold having a ridge and groove pattern through mineralization analysis.
Figure 9B:
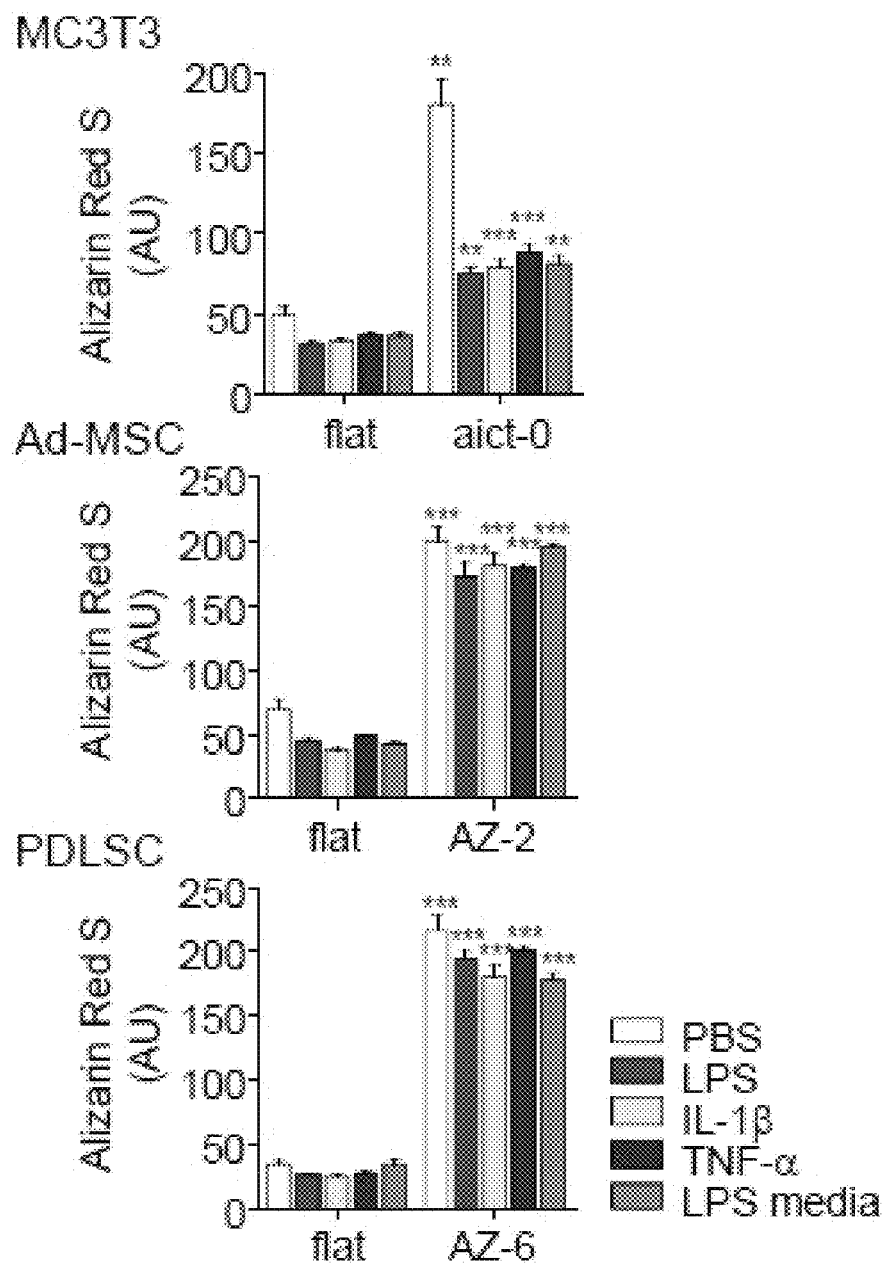
FIG. 9B represents bar graphs illustrating the result of FIG. 9A.

In the differentiation into osteoblasts by the scaffold having a ridge and groove pattern of the present disclosure, in order to confirm the influence of the inflammation generally caused by trauma or the insertion of a prosthesis, i.e., the influence of the inflammatory factor on the osteoblast differentiation, the degree of differentiation of each cell that induces osteoblast differentiation was confirmed by the method of Experimental Example 1-4. The cells were analyzed by Image J following Alizarin Red S staining, as described in Experimental Example 2-1-1. The results were calculated by interpolation. The result is illustrated in FIG. 9A, and the graph is illustrated in FIG. 9B.

As illustrated in FIG. 9, when cells are cultured on the flat scaffold control group, the osteoblast differentiation is suppressed by inflammatory cytokine. However, it was confirmed that the cells of the scaffold having a ridge and groove pattern of the present disclosure (TPT; aict-0, AZ-2, AZ-6) significantly overcome the inhibitory effect on osteoblast differentiation by the inflammatory factors without regard to cell types. This shows that the specific ridge and groove pattern overcomes the inhibitory effect on osteoblast differentiation by inflammation, and ultimately has an effective bone regeneration effect.

Figure 10A:
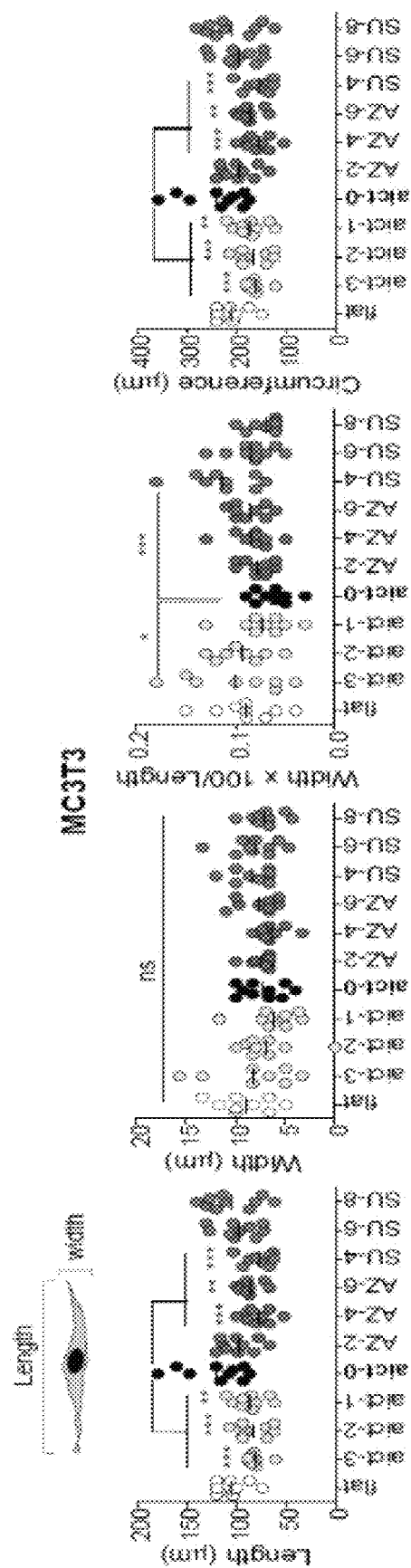
FIG. 10A represents bar graphs illustrating the physical feature of osteoblasts differentiated on a scaffold having a ridge and groove pattern through SEM observation using MC3T3 cells.
Figure 10B:
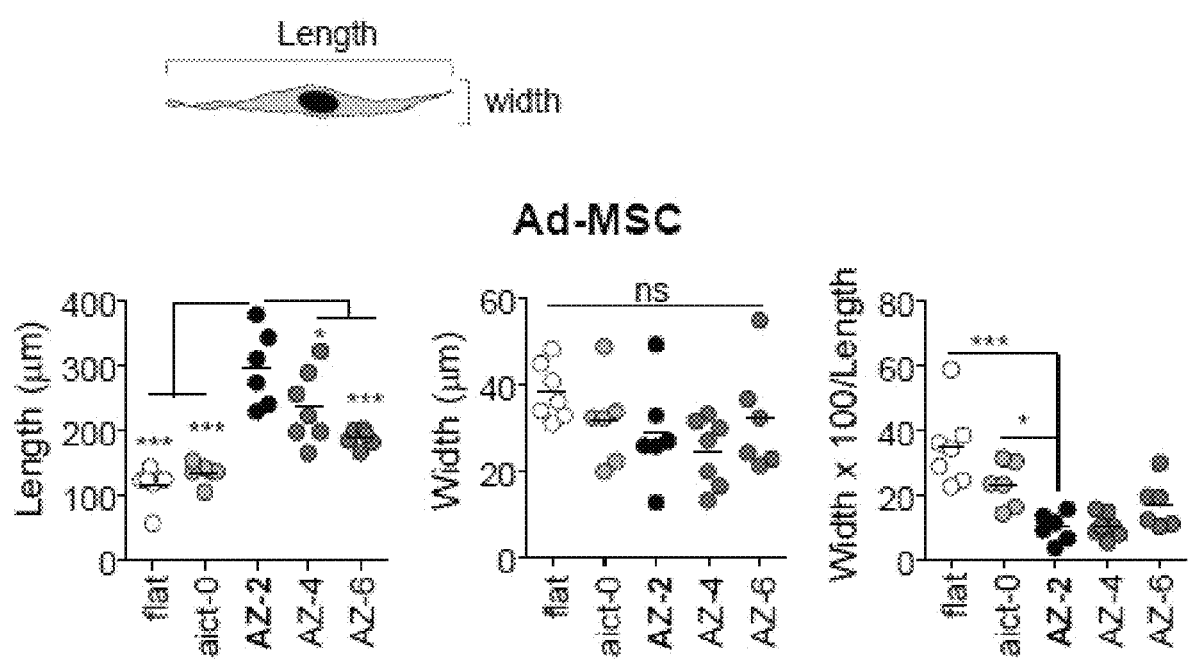
FIG. 10B represents bar graphs illustrating the physical feature of osteoblasts differentiated on a scaffold having a ridge and groove pattern through SEM observation using Ad-MSC cells.
Figure 10C:
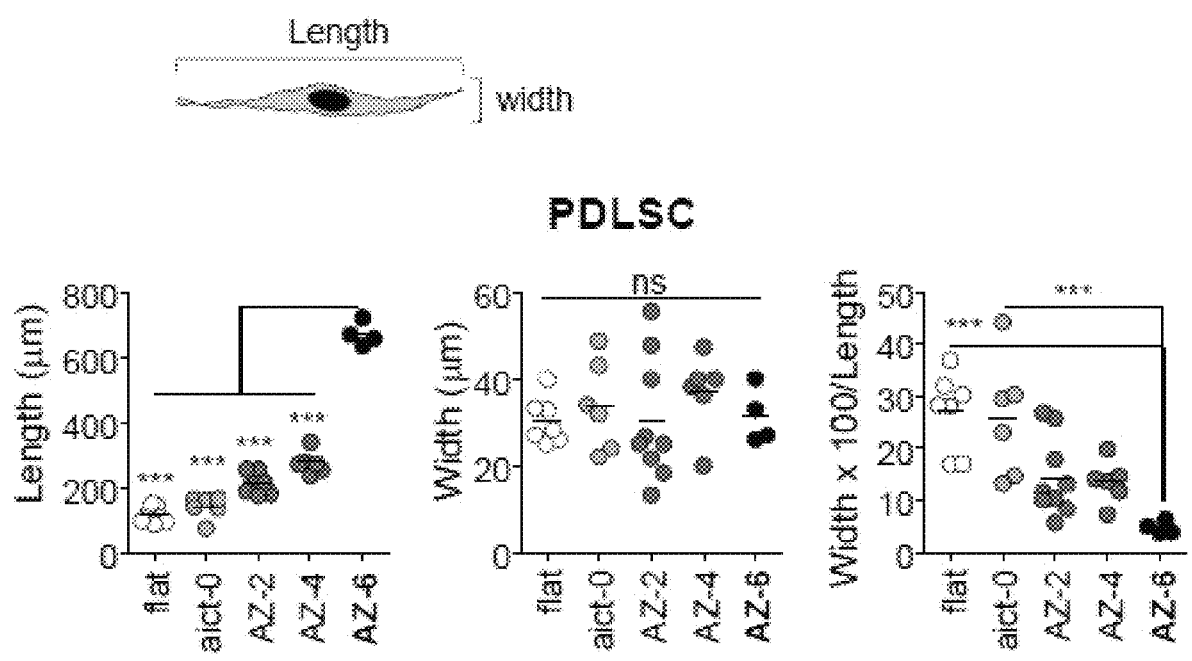
FIG. 10C represents bar graphs illustrating the physical feature of osteoblasts differentiated on a scaffold having a ridge and groove pattern through SEM observation using PDLSC cells.

2-2. Confirmation of Physical Characteristics of Differentiated Osteoblasts by a Scaffold Having a Ridge and Groove Pattern of the Present Disclosure Through SEM Observation In order to observe the arrangement of the cells cultured on the scaffold having the ridge and the groove pattern of the present disclosure and the singularity of an outward form, each cell cultured in Experimental Example 1-1 was dispensed on a flat scaffold or a scaffold having a ridge and groove pattern, and was cultured for two days. Subsequently, the cells attached to the surface of each scaffold were then fixed in a modified Karnovsky's fixative consisting of 2% paraformaldehyde and 2% glutaraldehyde (Sigma-Aldrich) dissolved in PBS for 4 hours. Thereafter, the sample was dehydrated by ethanol continuous culture (50-60-70-80-90-100%, treated for 5 to 10 minutes each), and hexamethyldisilazane (Sigma-Aldrich) was treated for 15 minutes. Subsequently, the sample was sputter-coated with gold to be observed with FE-SEM(S-4800). The resulting image was analyzed with Image J, and then the length (L), width (W) and W/L ratio (width×100/length) or circumference were measured. In addition, in order to observe the outline portion of the cells, a flat scaffold or a membrane portion of a cell attached to a scaffold having a ridge and groove pattern was mainly observed. The outline portion of the cell membrane was analyzed by computer-assisted morphometry (Rhinoceros 3D, Seattle, Wash., USA). The results for MC3T3 cells are shown in FIG. 10A, the results for Ad-MSC cells are shown in FIG. 10B, and the results for PDLSC are shown in FIG. 10C.

As illustrated in FIG. 10, it was confirmed that there was almost no change in the length of the flat scaffold, and that the width varied depending on the cell type. However, it was confirmed that the scaffold having a ridge and groove pattern of the present disclosure showed that the cell length is elongated to the maximum according to the cell type, but the width was barely changed. That is, it was confirmed that the W/L ratio increased almost proportionally with the elongation of the cell length. Specifically, the scaffold having a ridge and groove pattern of the present disclosure showed the following lengths of elongation (mean±standard error of mean [SEM]): for MC3T3, flat scaffold (flat)=105.1±5.48 µm, aict-3=80.9±3.19 µm, aict-2=82.0±5.54 µm, aict- 1=86.2±5.31 µm, aict-0=120.3±9.91 µm, AZ-2=97.7±5.65 µm, AZ-4=77.9±4.89 µm, AZ-6=86.7±3.70 µm, SU-4=77.1±4.87 µm, SU-6=97.7±4.63 µm, and SU-8=104.3±8.48 µm; for Ad-MSC, flat scaffold=117.3±10.37 µm, aict-0=136.3±6.61 µm, AZ-2=297.2±24.11 µm, AZ-4=237.1±21.19 µm, and AZ-6=189.1±5.56 µm; and for PLDSC, flat scaffold=117.3±9.57 µm, aict-0=142.1±13.92 µm, AZ-2=217.5±13.92 µm, AZ-4=277.8±14.30 µm, and AZ-6=673.3±18.39 µm).

This means that the degree of cell elongation changes in response to the surface form (topography) of the scaffold on which the cell characteristics are cultured. In particular, this suggests the induction of elongation of cells by inducing tensile stress necessary for osteoblast differentiation by a scaffold having a specific ridge and groove pattern.

2-3. Expression Analysis of Osteoblast Differentiation-related Gene Through Quantitative RT-PCR Performance Cells were collected and RNA was extracted (RNeasy Mini kit, Qiagen, Valencia, Calif., USA) after 0, 1, 5, and 10 days while MC3T3 was differentiated into osteoblasts as described in Experimental Example 1-1. cDNA was synthesized therefrom. The synthesized cDNA was analyzed by quantitative PCR with Exicycler™ 96 Quantitative Real-Time PCR System (Bioneer) using qPCR PreMix (Bioneer, Daejeon, Republic of Korea).

Figure 11A:
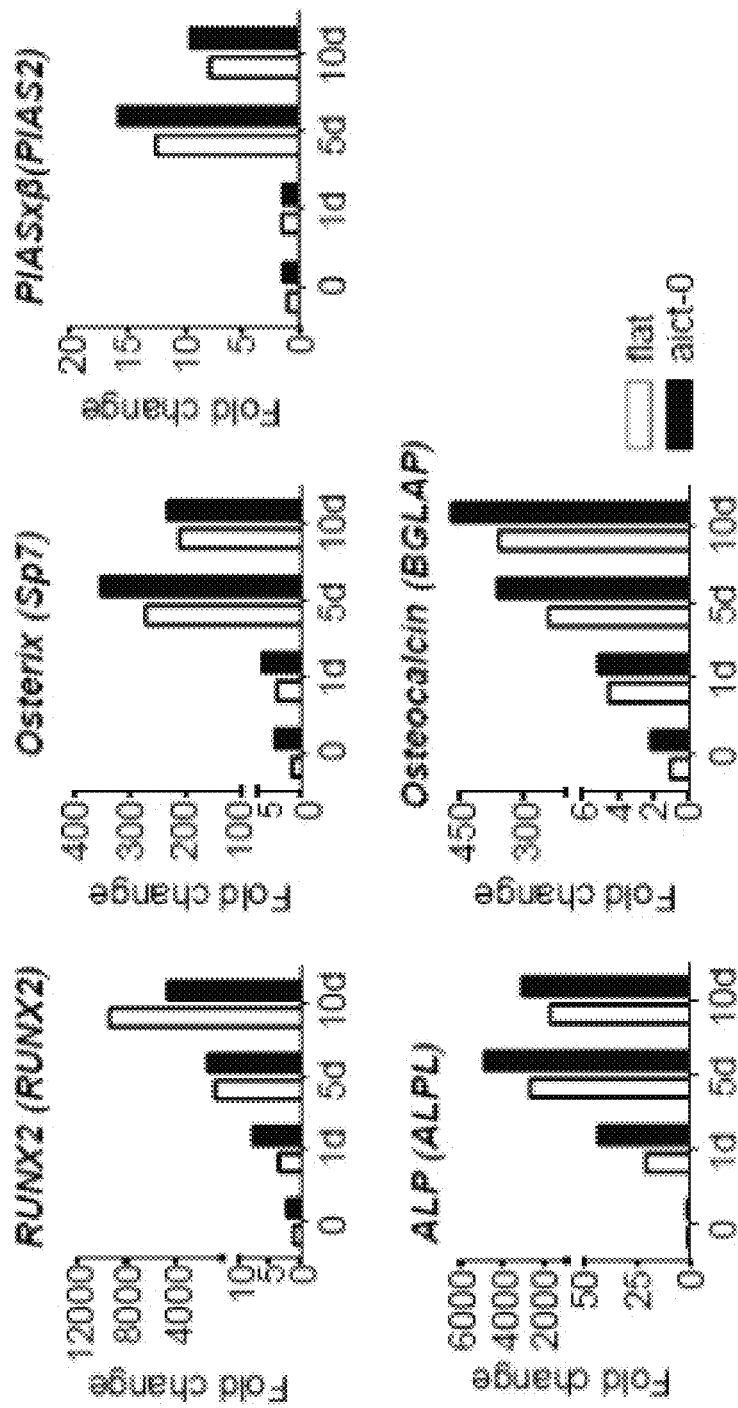
FIG. 11A represents bar graphs illustrating the expression levels of differentiation-related genes by a scaffold having a ridge and groove pattern through quantitative RT-PCR analysis. Specifically.

In addition, using a primer set disclosed in Table 2 below, the expression of genes associated with osteoblast differentiation such as Runx2 (runt-related transcription factor 2), ALPL (alkaline phosphatase gene), SP7 (osterix), BGLAP (osteocalcin), PIAS (protein inhibitor of activated STAT) was analyzed, and the results are illustrated in FIG. 11A.

TABLE 2

| Genes | Remarks | SEQ ID NOS. | Sequence listing |
|---|---|---|---|
| Runx2 | Forward direction | 1 | 5'-CGGCCCTCCCTGA ACTCT-3' |
| | Reverse direction | 2 | 5'-TGCCTGCCTGGGA TCTGTA-3' |
| ALPL | Forward direction | 3 | 5'-TTGTGCCAGAGAA AGAGAGAG-3' |
| | Reverse direction | 4 | 5'-GTTTCAGGCATTT TTCAAG-3' |
| SP7 | Forward direction | 5 | 5'-CCCTTCTCAAGCA CCAATGG-3' |
| | Reverse direction | 6 | 5'-AGGGTGGGTAGTC ATTTGCATAG-3' |
| BGLAP | Forward direction | 7 | 5'-CTGACAAAGCCTT CATGTCCAA-3' |
| | Reverse direction | 8 | 5'-GCGGGCGAGTCTG TTCACTA-3' |
| PIAS | Forward direction | 9 | 5'-CCTTATTCCAGTT GATCCCAGT-3' |
| | Reverse direction | 10 | 5'-TATGACCCCTGTC TCACTCCT-3' |
| GAPDH | Forward direction | 11 | 5'-CAAGGTCATCCAT GACAACTTTG-3' |
| | Reverse direction | 12 | 5'-GGCCATCCACAGT CTTCTGG-3' |

Figure 11B:
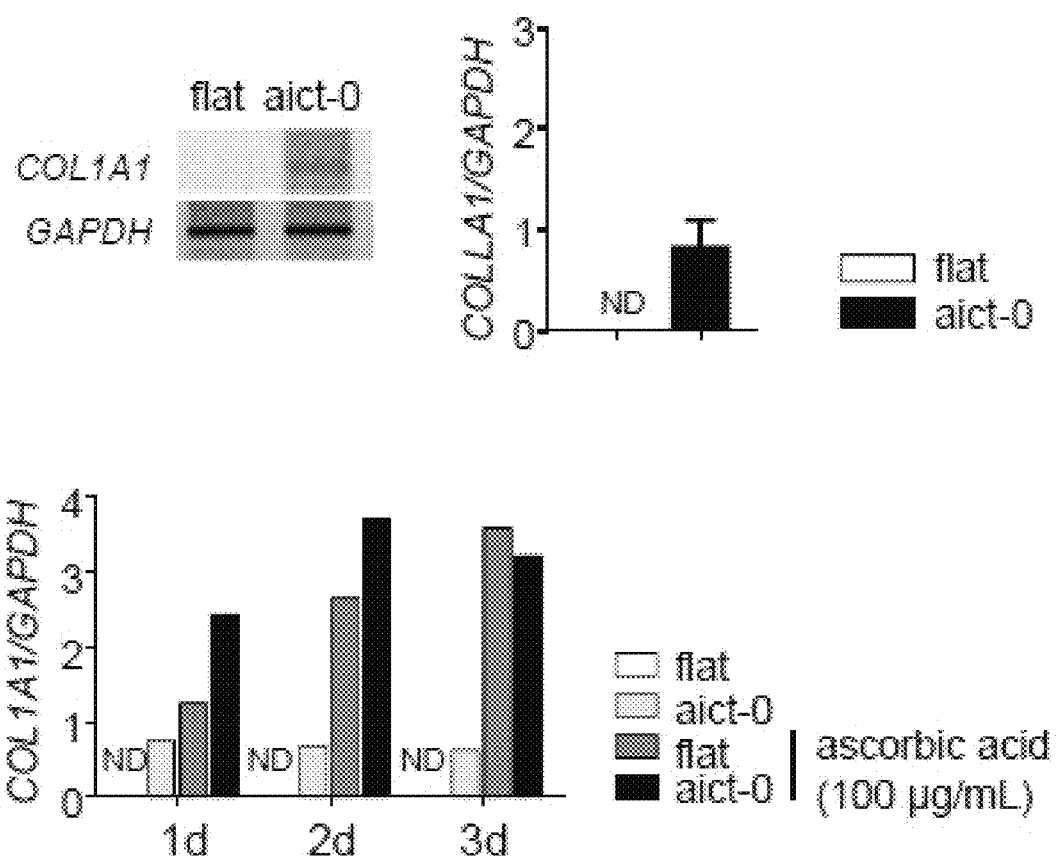
FIG. 11B represents bar graphs illustrating the expression levels of differentiation-related genes by a scaffold having a ridge and groove pattern through quantitative RT-PCR analysis. Specifically.

In addition, when 1, 2, and 3 days elapsed after MC3T3 cells were cultured on a flat scaffold or a scaffold (aict-0) having a ridge and groove pattern of the present disclosure with addition of AA (100 µg/mL), the expression level of COL1A1 was measured. The results are illustrated in FIG. 11B. The values illustrated in each figure were normalized by expression of the control group gene GAPDH, and the experiments on a flat scaffold were performed with a control group.

As illustrated in FIG. 11A, it was confirmed that unlike a flat scaffold, RUNX2 showed an increase in the expression level at the early stage of osteoblast differentiation in the scaffold having a groove pattern of the present disclosure and a decrease in the expression level of RUNX2 at the late stage of osteoblast differentiation. It was confirmed when the osteoblast differentiation is sufficiently made, the expression levels of ALP, SP7 and BGLAP were increased.

In addition, as illustrated in FIG. 11B, as a result of analyzing type 1 collagen, which is a major factor of osteoblast differentiation, with qRT-PCR, the osteoblast differentiation was induced without adding AA. However, it was confirmed that when AA was added, the expression levels of type 1 collagen (COL1A1) and type 3 collagen mRNA were increased so that the osteoblast differentiation was further increased.

This illustrates that the scaffold having a ridge and groove pattern of the present disclosure controls the expression in the transcription step to promote osteoblast differentiation.

2-4. Confirmation of the Influence of Reactive Oxygen Species (ROS) Through Immunofluorescence Staining It is well known that the production of reactive oxygen species is promoted by neutrophils at the site of inflammation and excessive reactive active oxygen suppresses the osteoblast differentiation. Thus, the level change of active oxygen according to the culture of precursor cells of osteoblasts in the patterned scaffold of the present disclosure was measured.

Figure 12A:
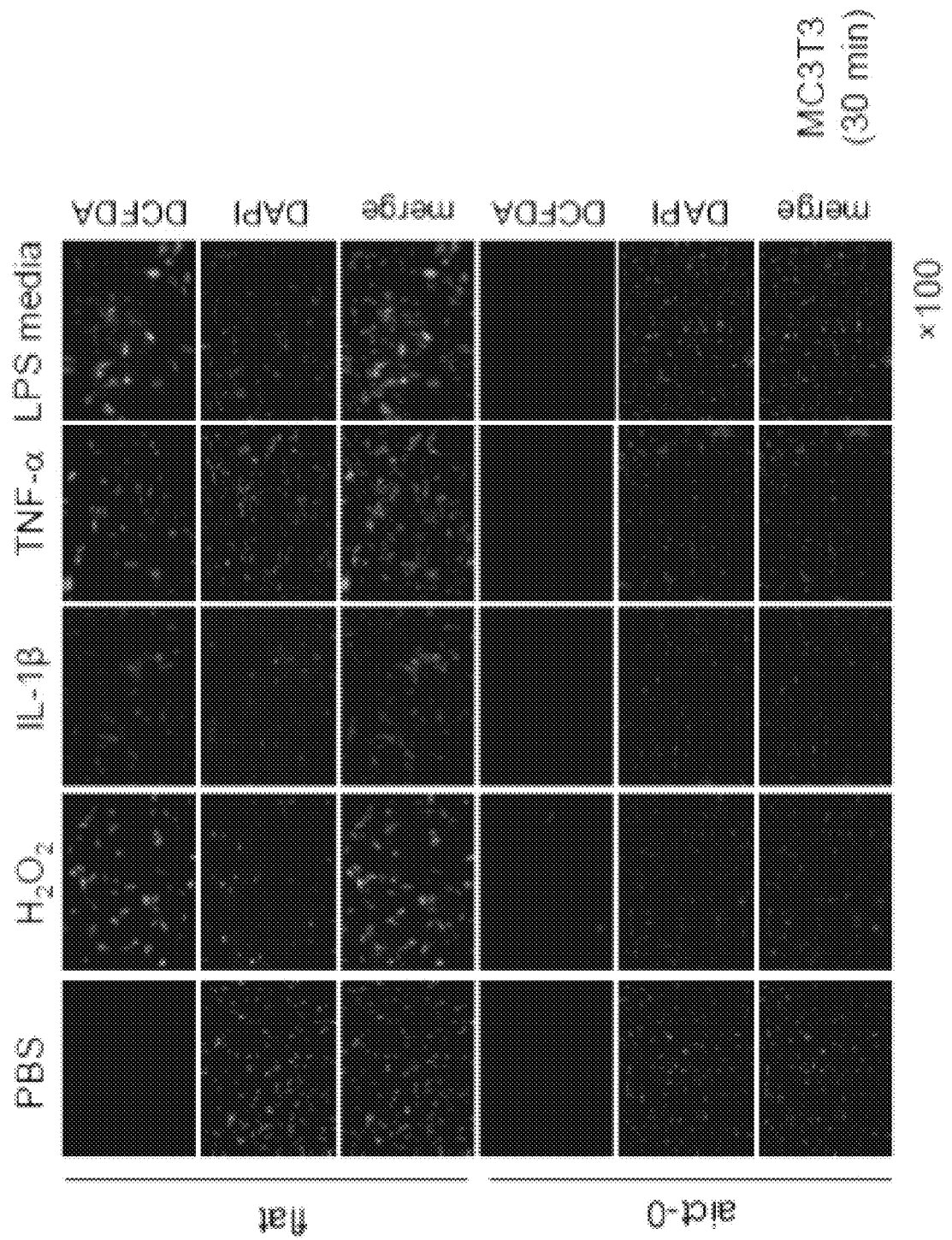
FIG. 12A represents photographs illustrating the effect of reactive oxygen species (ROS) on a scaffold having a ridge and groove pattern through immunofluorescence staining.
Figure 12B:
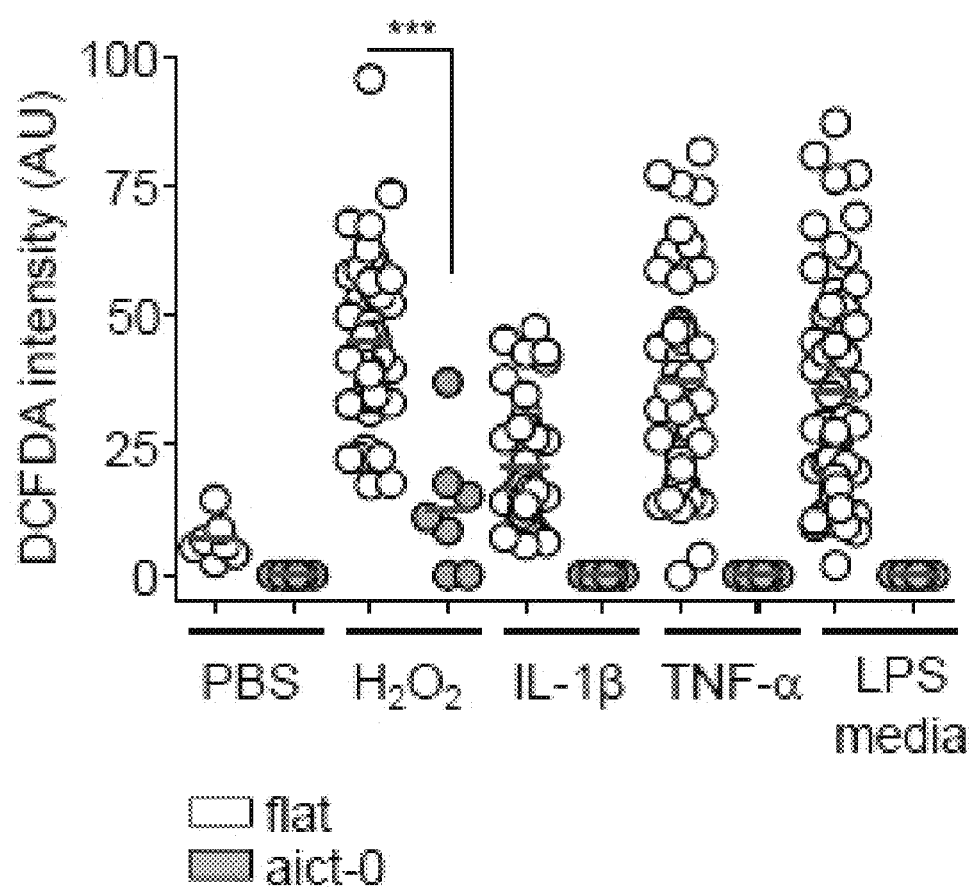
FIG. 12B represents a graph illustrating the result of FIG. 12A.

First, MC3T3 was differentiated into osteoblasts as in Experimental Example 1-1, and MC3T3 grown on a flat scaffold or a scaffold (aict-0) having a ridge and groove pattern of the present disclosure was treated with splenocyte culture solution of a mouse treated for 3 days with $H_2O_2$ (2 mM), TNF-α (10 ng/mL), IL-1β (10 ng/mL) and LPS (1 µg/mL), respectively. The degree of generation of active oxygen was analyzed by using a staining method. Specifically, for the measurement of reactive oxygen, the cells were washed with PBS, cultured in 10 µM DCFDA at 37° C. for 30 minutes, and contrast stained with DAPI (4',6-diamidino-2-phenylindole, Sigma-Aldrich). The stained images were obtained with a fluorescence microscope (Olympus) and images were analyzed with ProgRes Capture Pro software (Jenoptik, Jena, Germany). The results are illustrated in FIGS. 12A and 12B.

As illustrated in FIG. 12, it was confirmed that the generation of active oxygen was suppressed in the scaffold (aict-0) having a groove pattern of the present disclosure, unlike the flat scaffold on which the experiment was performed as a control group. Accordingly, it can be understood that the scaffold having a groove pattern of the present disclosure enhances the osteoblast differentiation by suppressing the active oxygen generated by the inflammatory environment in the context that the osteoblast formation by a groove pattern of the present disclosure occurs well under inflammatory conditions. In other words, changes in cell activity and inhibition of reactive oxygen species due to mechanical stresses induce the expression of osteoblast-related genes, eventually inducing osteoblast differentiation.

EXPERIMENTAL EXAMPLE 3

Confirmation of the In Vivo Bone Regeneration Effect by the Scaffold Having a Ridge and Groove Pattern of the Present Disclosure 3-1. Experimental Animals and their Breeding 8-week-old male Sprague Dawley rats (220-240 g, Orient Bio Inc., Seongnam, Republic of Korea) were raised in an aseptic environment in the animal room of Seoul National University College of Dentistry. All experiments were conducted under the approval of the Animal Experimental Ethics Committee of the Institute of Laboratory Animal Resources Seoul National University (#SNU-160912-18-1). All specimens were sterilized prior to performing transplantation using ethylene oxide gas.

3-2. Preparation of a Rat Calvarial Defect Model and Implantation of a Scaffold Having a Ti-coated Ridge and Groove Pattern of the Present Disclosure Rat critical-sized calvarial defect was used to measure bone regeneration ability by a scaffold having the Ti-coated ridge and groove pattern of the present disclosure.

Specifically, the rats raised in Experimental Example 3-1 were anesthetized by intraperitoneal injection of a mixture of zolazepam and tiletamine (30 mg/kg, Zoletil; Virbac Laboratories, Carros, France) and xylazine (Rompun; Bayer, Leverkusen, Germany) 10 mg/kg. Subsequently, the hair on the back surface of the skull was removed, and the corresponding area was disinfected.

A medium-sized incision of 5 cm was made on the site and a bone defect of 8 mm diameter was made using a trephine attached to an electric drill (TPHB-B8; Osung, Gumi, Republic of Korea). The skull disc was then removed. For the transplantation, the scaffold (12 mm diameter) having the Ti-coated ridge and groove pattern prepared in the Example 1-2-1 was placed in the defect site. The scaffold was then covered with the periosteum, sealed, and fixed, and the skin was covered with a 4-0 silk suture.

3-3. Confirmation of Bone Regeneration Effect by a Scaffold Having Ti-coated Ridge and Groove Pattern of the Present Disclosure by High-resolution Tomography (Micro-computed Tomography)

In the manner described in Experimental Example 3-2, a scaffold having the Ti-coated ridge and bone pattern of the present disclosure was implanted in a rat critical-sized calvarial defect model. The rat was euthanized using carbon dioxide gas after 12 weeks of implanting.

Figure 13A:
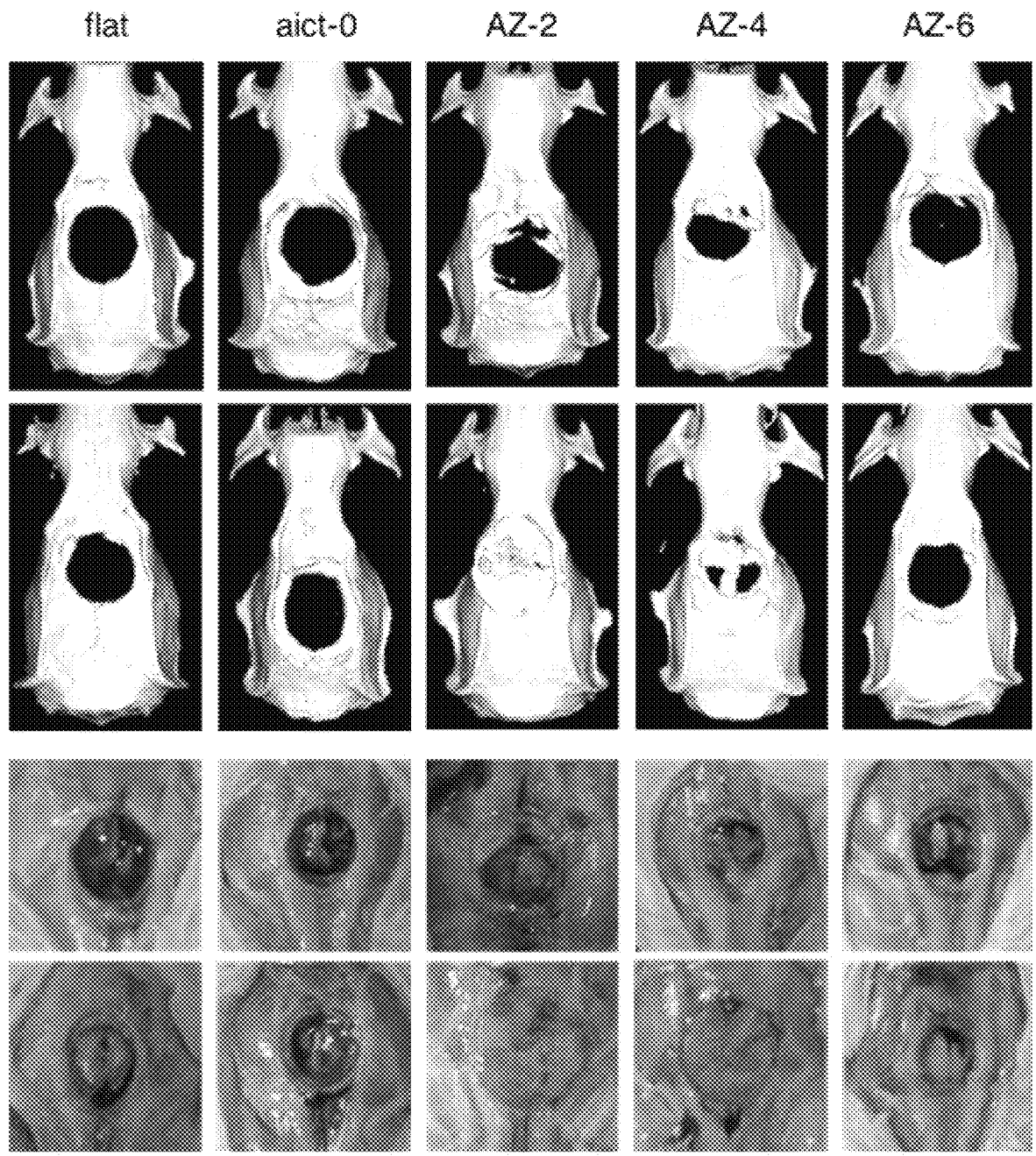
FIG. 13A represents photographs illustrating the effect of bone regeneration by a scaffold having a Ti-coated ridge and groove pattern through a high-resolution tomography (Micro-computed tomography). Specifically, FIG. 13A confirms bone regeneration in the skull defect in a rat critical-sized calvarial defect model after transplanting a Ti-coated groove pattern.

Thereafter, new bone formation was confirmed by a micro CT scanner (Quantum GX In-vivo Micro-CT; PerkinElmer, Waltham, Mass., USA) of a 90 kV and 88 µA X-ray tube. It was imaged with a scanner having a high resolution scan mode by setting a field of vision of 72 mm, an initial voxel size of 144 µm, and a voxel size of 9 µm after a reconstructed sub-volume. The imaged data were reconstructed using an OsiriX Lite Image software (ver. 5.0.2; Pixmeo, Bernex, Switzerland) having a threshold value for removing soft tissues and observing the density of bones. The results are illustrated in FIG. 13A.

Figure 13B:
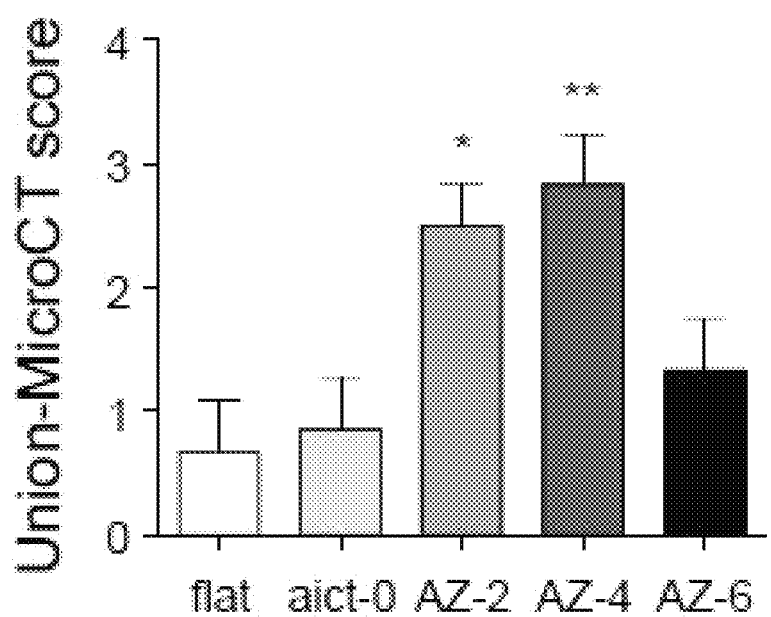
FIG. 13B represents a bar graph illustrating the changes in bone bridges and unions.

In addition, the bone bridge and union changes in the skull defect in the rat calvarial defect model after transplanting the Ti-coated groove pattern of the present disclosure are classified into five categories (0, no bone formation in the defect; 1, almost no fragments spread from the defect; 2, formation of a bone bridge only at the defect boundary; 3, formation of a bone bridge partially at the defect; and 4 formation of a bone bridge at the entire portion of the defect within the longest length (8 mm)). The results are illustrated in FIG. 13B.

As illustrated in FIG. 13, it was confirmed that bone regeneration was significantly occurred in the scaffolds having a ridge and groove pattern of the present disclosure, especially AZ-2 and AZ-4, as compared with a flat scaffold used as a control group. This shows that the scaffold having the Ti-coated ridge and groove pattern of the present disclosure induces osteoblast differentiation of cells, and ultimately has an excellent bone regeneration effect.

3-4. Confirmation of Bone Regeneration Effect by the Scaffold Having Ti-coated Groove Pattern of the Present Disclosure Through Histological Analysis Histological analysis was performed to more clearly confirm the bone regeneration effect confirmed through the Experimental Example 3-3. Specifically, in the manner described in the Experimental Example 3-2, a scaffold having a Ti-coated ridge and groove pattern of the present disclosure was implanted into a rat calvarial defect model, and after 12 weeks, it was sacrificed for histological analysis. The defect around tissues was then fixed with 10% (v/v) neutral-buffered formalin for 4 days and calcium was removed with a decalcifier (Leica Decalcifier; Leica Biosystems, Nussloch, Germany).

The paraffin wax was then pushed into the rostral faces. The paraffin wax sample was cut to a 4 µm-thick slice in the longitudinal direction, and then paraffin was removed with xylene and hydrated with alcohol. H & E staining was then performed in a manner commonly used in the pertinent technical field, and then observed using an Aperio ImageScope (Leica Biosystems). The results are illustrated in FIG. 14.

Figure 14:
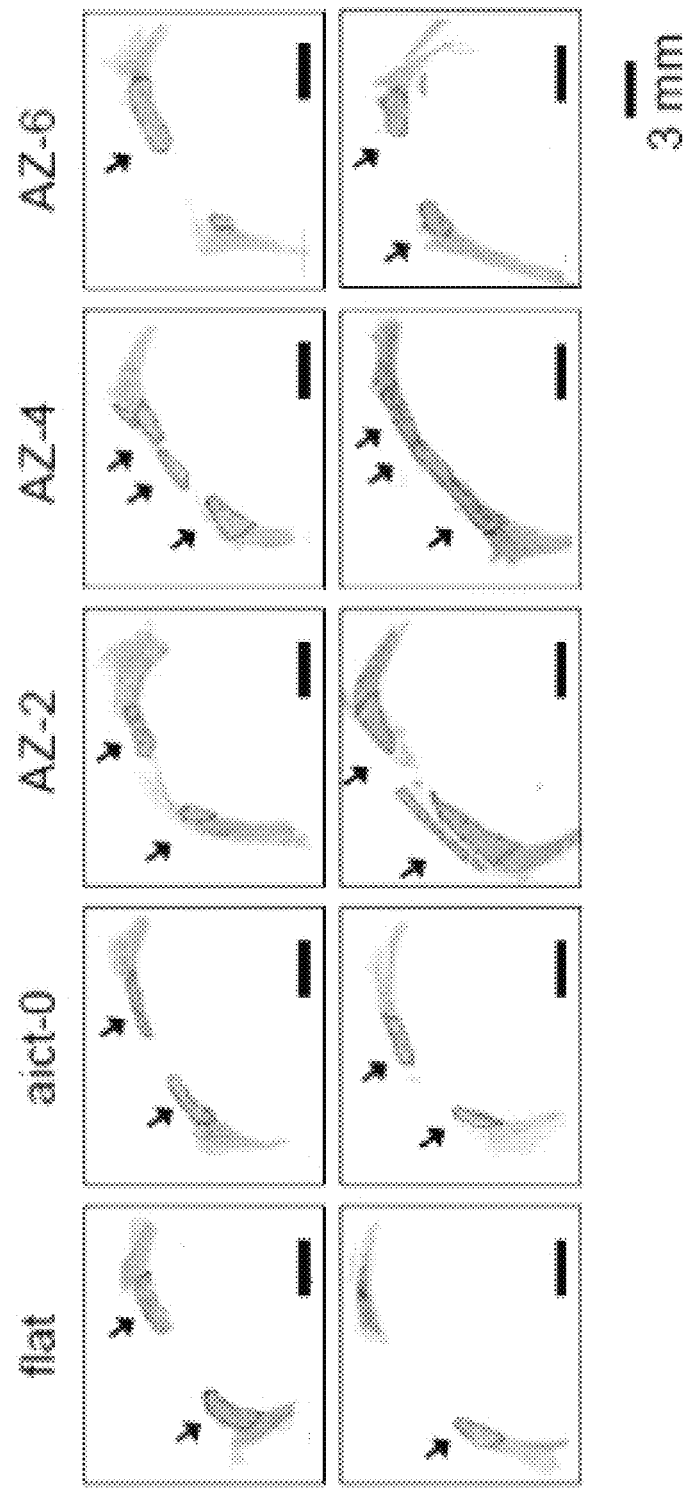
FIG. 14 represents photographs illustrating the effect of bone regeneration by a scaffold having a Ti-coated groove pattern through histological analysis.

As illustrated in FIG. 14, it was confirmed that the bone regeneration was significantly occurred in the scaffolds having a ridge and groove pattern of the present disclosure, particularly AZ-2 and AZ-4, compared with the flat scaffold. In addition, when the scaffold having a ridge and groove pattern of the present disclosure is used, the results of the above experiment show that the osteoblast differentiation is induced in the cells without the supplementation of additional osteogenic factors.

EXPERIMENTAL EXAMPLE 4

Statistical Analysis

All data were expressed as mean and standard error of mean (SEM). Data were compared using two-tailed Student's t-test or one-way ANOVA followed by Dunnett's post hoc test. P value of less than 0.05 was determined to be statistically significant. Statistical analysis was performed using GraphPad Prism software ver. 5.01 (GraphPad Software, La Jolla, Calif.).

To sum up, the culture scaffold of the present disclosure has an optimal pattern depending on the type of stem cells or precursor cells, thereby improving the osteoblast differentiation potency. In particular, it has a feature of showing an excellent osteoblast differentiation even if only a small amount of supplementary factors inducing osteoblast differentiation is added. Furthermore, the potency of osteoblast differentiation is not greatly influenced by the change in cell density and by the inflammatory factors that inhibit osteoblast differentiation. Thus, there is an advantage in that the efficiency of osteoblast differentiation efficiency is high. Accordingly, the culture scaffold of the present disclosure having excellent bone regeneration ability can be utilized in various biomedical and medical fields such as dental implants, artificial joints and trauma fixation devices.

What is claimed is:

1. A method for differentiating osteoblast precursor cells, adipose tissue-derived mesenchymal stem cells, or periodontal ligament stem cells into osteoblasts, comprising:
   (a) inoculating and culturing at least one type of cells selected from the group consisting of: osteoblast precursor cells, adipose tissue-derived mesenchymal stem cells, and periodontal ligament stem cells in a culture scaffold comprising a ridge and a groove, wherein when the at least one type of cells comprises osteoblast precursor cells, the culture scaffold comprises the ridge having a width from 0.1 μm to 3 μm and the groove having a width from 1.5 μm to 7 μm, wherein when the at least one type of cells comprises adipose tissue-derived mesenchymal stem cells, the culture scaffold comprises the ridge having a width from 0.1 μm to 3 μm and the groove having a width from 0.76 μm to 7 μm, or wherein when the at least one type of cells comprises periodontal ligament stem cells, the culture scaffold comprises the ridge having a width from 0.5 μm to 5 μm and the groove having a width from 1.5 μm to 7 μm; and (b) differentiating the at least one type of cells into osteoblasts, wherein the at least one type of cells is differentiated into osteoblasts under inflammatory conditions.

2. The method according to claim 1, wherein the culture scaffold comprises at least one agent selected from the group consisting of: trimethylolpropane propoxylate triacrylate (TPT), tripropylene glycol diacrylate (TPD), triethylene glycol dimethacrylate (TGD), triarylcyanate (TAC), trimethylolpropane trimethacrylate (TPTM), polycaprolactone (PCL), collagen, gelatin, hyaluronic acid, keto acid, laminin, keratin, alginate, fibronetin, polyglycolic acid (PGA), poly lactic acid (PLA), polylactic acid-glycolic acid copolymer (PLGA), polyamino acid, polyanhydride, polyorthoester, polyurethane, titanium (Ti), aluminum (Al), vanadium (V), titanium alloy, stainless steel, cobalt alloy, nickel-titanium alloy (NiTi), and a combination thereof.

3. The method according to claim 1, wherein the at least one type of cells is osteoblast precursor cells, and the culture scaffold comprises the ridge having a width from 0.5 μm to 2 μm and the groove having a width from 1.8 μm to 4 μm.

4. The method according to claim 1, wherein the at least one type of cells is adipose tissue-derived mesenchymal stem cells, and the culture scaffold comprises the ridge having a width from 0.5 μm to 2 μm and the groove having a width from 1.8 μm to 4 μm.

5. The method according to claim 1, wherein the at least one type of cells is periodontal ligament stem cells, and the culture scaffold comprises the ridge having a width from 2 μm to 2.83 μm and the groove having a width from 2 μm to 6 μm.

6. A method for differentiating periodontal ligament stem cells into osteoblasts, comprising:

(a) inoculating and culturing periodontal ligament stem cells in a culture scaffold comprising a ridge and a groove, wherein the culture scaffold comprises the ridge having a width from 2 μm to 2.83 μm and the groove having a width from 2 μm to 6 μm; and (b) differentiating the at least one type of cells into osteoblasts.

7. The method according to claim 6, wherein the culture scaffold comprises at least one agent selected from the group consisting of: trimethylolpropane propoxylate triacrylate (TPT), tripropylene glycol diacrylate (TPD), triethylene glycol dimethacrylate (TGD), triarylcyanate (TAC), trimethylolpropane trimethacrylate (TPTM), polycaprolactone (PCL), collagen, gelatin, hyaluronic acid, keto acid, laminin, keratin, alginate, fibronetin, polyglycolic acid (PGA), poly lactic acid (PLA), polylactic acid-glycolic acid copolymer (PLGA), polyamino acid, polyanhydride, polyorthoester, polyurethane, titanium (Ti), aluminum (Al), vanadium (V), titanium alloy, stainless steel, cobalt alloy, nickel-titanium alloy (NiTi), and a combination thereof.

* * * * *

SEQUENCE LISTING

<160> NUMBER OF SEQ ID NOS: 12

<210> SEQ ID NO 1
<211> LENGTH: 18
<212> TYPE: DNA
<213> ORGANISM: Artificial Sequence
<220> FEATURE:
<223> OTHER INFORMATION: forward primer for Runx2

<400> SEQUENCE: 1
cggccctccc tgaactct                18

<210> SEQ ID NO 2
<211> LENGTH: 19
<212> TYPE: DNA
<213> ORGANISM: Artificial Sequence
<220> FEATURE:
<223> OTHER INFORMATION: reverse primer for Runx2

<400> SEQUENCE: 2
tgcctgcctg ggatctgta               19

<210> SEQ ID NO 3
<211> LENGTH: 21
<212> TYPE: DNA
<213> ORGANISM: Artificial Sequence
<220> FEATURE:
<223> OTHER INFORMATION: forward primer for ALPL

<400> SEQUENCE: 3
ttgtgccaga gaaagagaga g            21

<210> SEQ ID NO 4
<211> LENGTH: 19
<212> TYPE: DNA
<213> ORGANISM: Artificial Sequence
<220> FEATURE:
<223> OTHER INFORMATION: reverse primer for ALPL

<400> SEQUENCE: 4
gtttcaggca tttttcaag               19

<210> SEQ ID NO 5
<211> LENGTH: 20
<212> TYPE: DNA
<213> ORGANISM: Artificial Sequence
<220> FEATURE:
<223> OTHER INFORMATION: forward primer for SP7

<400> SEQUENCE: 5
cccttctcaa gcaccaatgg              20

<210> SEQ ID NO 6
<211> LENGTH: 23
<212> TYPE: DNA
<213> ORGANISM: Artificial Sequence
<220> FEATURE:
<223> OTHER INFORMATION: reverse primer for SP7

<400> SEQUENCE: 6
agggtgggta gtcatttgca tag          23

<210> SEQ ID NO 7
<211> LENGTH: 22
<212> TYPE: DNA
<213> ORGANISM: Artificial Sequence

```
<220> FEATURE:
<223> OTHER INFORMATION: forward primer for BGLAP

<400> SEQUENCE: 7
ctgacaaagc cttcatgtcc aa                                          22

<210> SEQ ID NO 8
<211> LENGTH: 20
<212> TYPE: DNA
<213> ORGANISM: Artificial Sequence
<220> FEATURE:
<223> OTHER INFORMATION: reverse primer for BGLAP

<400> SEQUENCE: 8
gcgggcgagt ctgttcacta                                             20

<210> SEQ ID NO 9
<211> LENGTH: 23
<212> TYPE: DNA
<213> ORGANISM: Artificial Sequence
<220> FEATURE:
<223> OTHER INFORMATION: forward primer for PIAS

<400> SEQUENCE: 9
ccttattcca gttgatcccc agt                                         23

<210> SEQ ID NO 10
<211> LENGTH: 21
<212> TYPE: DNA
<213> ORGANISM: Artificial Sequence
<220> FEATURE:
<223> OTHER INFORMATION: reverse primer for PIAS

<400> SEQUENCE: 10
tatgacccct gtctcactcc t                                           21

<210> SEQ ID NO 11
<211> LENGTH: 23
<212> TYPE: DNA
<213> ORGANISM: Artificial Sequence
<220> FEATURE:
<223> OTHER INFORMATION: forward primer for GAPDH

<400> SEQUENCE: 11
caaggtcatc catgacaact ttg                                         23

<210> SEQ ID NO 12
<211> LENGTH: 20
<212> TYPE: DNA
<213> ORGANISM: Artificial Sequence
<220> FEATURE:
<223> OTHER INFORMATION: reverse primer for GAPDH

<400> SEQUENCE: 12
ggccatccac agtcttctgg                                             20
```